(12) United States Patent
Pasche et al.

(10) Patent No.: US 8,977,365 B2
(45) Date of Patent: Mar. 10, 2015

(54) ELECTRONIC SYSTEM FOR INFLUENCING CELLULAR FUNCTIONS IN A WARM-BLOODED MAMMALIAN SUBJECT

(75) Inventors: Boris Pasche, Mountain Brook, AL (US); Alexandre Barbault, Colmar (FR)

(73) Assignee: TheraBionic, LLC, Winston-Salem, NC (US)

( * ) Notice: Subject to any disclaimer, the term of this patent is extended or adjusted under 35 U.S.C. 154(b) by 134 days.

(21) Appl. No.: 13/573,104

(22) Filed: Aug. 22, 2012

(65) Prior Publication Data

US 2013/0079853 A1    Mar. 28, 2013

Related U.S. Application Data

(63) Continuation-in-part of application No. 12/450,450, filed on Oct. 29, 2009, now abandoned.

(30) Foreign Application Priority Data

Mar. 27, 2007 (EP) .................................. 07 006 320
Mar. 26, 2008 (EP) .................. PCT/EP2008/002379

(51) Int. Cl.
*A61N 5/00* (2006.01)
*A61N 1/40* (2006.01)
*A61N 5/02* (2006.01)

(52) U.S. Cl.
CPC .. *A61N 5/00* (2013.01); *A61N 1/40* (2013.01); *A61N 5/02* (2013.01); *A61N 5/022* (2013.01)
USPC ........ 607/115; 607/1; 607/2; 607/11; 607/15; 607/34

(58) Field of Classification Search
USPC ......... 607/1–2, 11, 15, 34, 115; 128/897–898
IPC ....... A61B 5/7228,5/00; A61F 2002/705; A61N 1/37223, 1/00, 1/36171, 1/36, 1/08
See application file for complete search history.

(56) References Cited

U.S. PATENT DOCUMENTS

| 4,649,935 A | 3/1987 | Charmillot et al. |
| 4,765,322 A | 8/1988 | Charmillot et al. |

(Continued)

FOREIGN PATENT DOCUMENTS

| EP | 0592851 A2 | 4/1994 |
| EP | 1070518 A2 | 1/2001 |

(Continued)

OTHER PUBLICATIONS

J. A. Koziol, M. Erman, B Pasche, R. Hajdukovic, M. M. Mitler: "Assessing a Changepoint in a Sequence of Repeated Measurements With Application to a Low-Energy Emission Therapy Sleep Study"; J. Applied Statistics 20, pp. 393-400, 1993.

(Continued)

*Primary Examiner* — Deborah Malamud
(74) *Attorney, Agent, or Firm* — Breiner & Breiner, L.L.C.

(57) ABSTRACT

An electronic system activatable by electrical power is described. The system is useful for influencing cellular functions or malfunctions in a warm-blooded mammalian subject. The system includes one or more controllable low energy HF (High Frequency) carrier signal generator circuits, one or more data processors for receiving control information, one or more amplitude modulation control generators and one or more amplitude modulation frequency control generators. The amplitude modulation frequency control generators are adapted to accurately control the frequency of the amplitude modulations to within an accuracy of at least 1000 ppm, most preferably to within about 1 ppm, relative to one or more determined or predetermined reference amplitude modulation frequencies.

18 Claims, 2 Drawing Sheets

(56) References Cited

U.S. PATENT DOCUMENTS

| | | | |
|---|---|---|---|
| 5,441,528 | A | 8/1995 | Chang et al. |
| 5,690,692 | A | 11/1997 | Fleming |
| 5,891,182 | A | 4/1999 | Fleming |
| 5,908,441 | A | 6/1999 | Bare |
| 6,167,304 | A | 12/2000 | Loos |
| 8,192,969 | B2 | 6/2012 | Tofani |
| 2005/0090732 | A1 | 4/2005 | Ivkov et al. |

FOREIGN PATENT DOCUMENTS

| | | |
|---|---|---|
| EP | 1070518 A3 | 1/2001 |
| EP | 0592851 B1 | 12/2001 |
| JP | 07-000546 A | 1/1995 |
| JP | 2006-167117 A | 6/2006 |
| RU | 2112563 C1 | 6/1998 |
| RU | 2127616 C1 | 3/1999 |

OTHER PUBLICATIONS

D. Amato, B. Pasche: "An Evaluation of the Safety of Low Energy Emission Therapy"; Compr Ther 19, pp. 242-247, 1993.

Higgs, M. Reite, A. Barbault, J. P. Lebet, C. Rossel, D. Amato, U. Dafni, B. Pasche: "Subjective and Objective Relaxation Effects of Low Energy Emission Therapy"; Stress Medicine 10, pp. 5-13, 1994.

M. Reite, L. Higgs, J. P. Lebet, A. Barbault, C. Rossel, N. Kuster, U. Dafni, D. Amato, B. Pasche: "Sleep Inducing Effect of Low Energy Emission Therapy"; Bioelectromagnetics 15, pp. 67-75, 1994.

J. P. Lebet, A. Barbault, C. Rossel, Z. Tomic, M. Reite, L. Higgs, U. Dafni, D. Amato, B. Pasche: Electroencephalographic Changes Following Low Energy Emission Therapy; Ann Biomed Eng 24, pp. 424-429, 1996.

B. Pasche, M. Erman, R. Hayduk, M. Mitler, M. Reite, L. Higgs, U. Dafni, D. Amato, C. Rossel, N. Kuster, A. Barbault, J. P. Lebet: "Effects of Low Energy Emission Therapy in Chronic Psychophysiological Insomnia"; Sleep 19, pp. 327-336, 1996.

T. L. Kelly, D. F. Kripke, R. Hayduk, D. Ryman, B. Pasche, A. Barbault: "Bright Light and LEET Effects on Circadian Rhythms, Sleep and Cognitive Performance"; Stress Medicine 13, pp. 251-258, 1997.

B. Pasche, A. Barbault: "Low-Energy Emission Therapy: Current Status and Future Directions"; In Bioelectromagnetic Medicine, P. J. Rosch, M. S. Markov (eds), pp. 321-327; Marcel Dekker, Inc., New York, New York, 2003.

L. Cordesses: "Direct Digital Synthesis: A Tool for Periodic Wave Generation (Part 1)"; IEEE Signal Processing Magazine, IEEE Service Center, Piscataway, New Jersey, US, vol. 21, No. 4, Jul. 2004, pp. 50-54, XP011115196.

Alexandre Barbault et al: Journal of Experimental & Clinical Cancer Research 2009, 28:51, Article entitled Amplitude-modulated electromagnetic fields for the treatment of cancer: Discovery of tumor-specific frequencies and assessment of a novel therapeutic approach, published Apr. 14, 2009.

FIG. 2    FB, 21.3.7    The dotted lines show different possibilities of embodiments
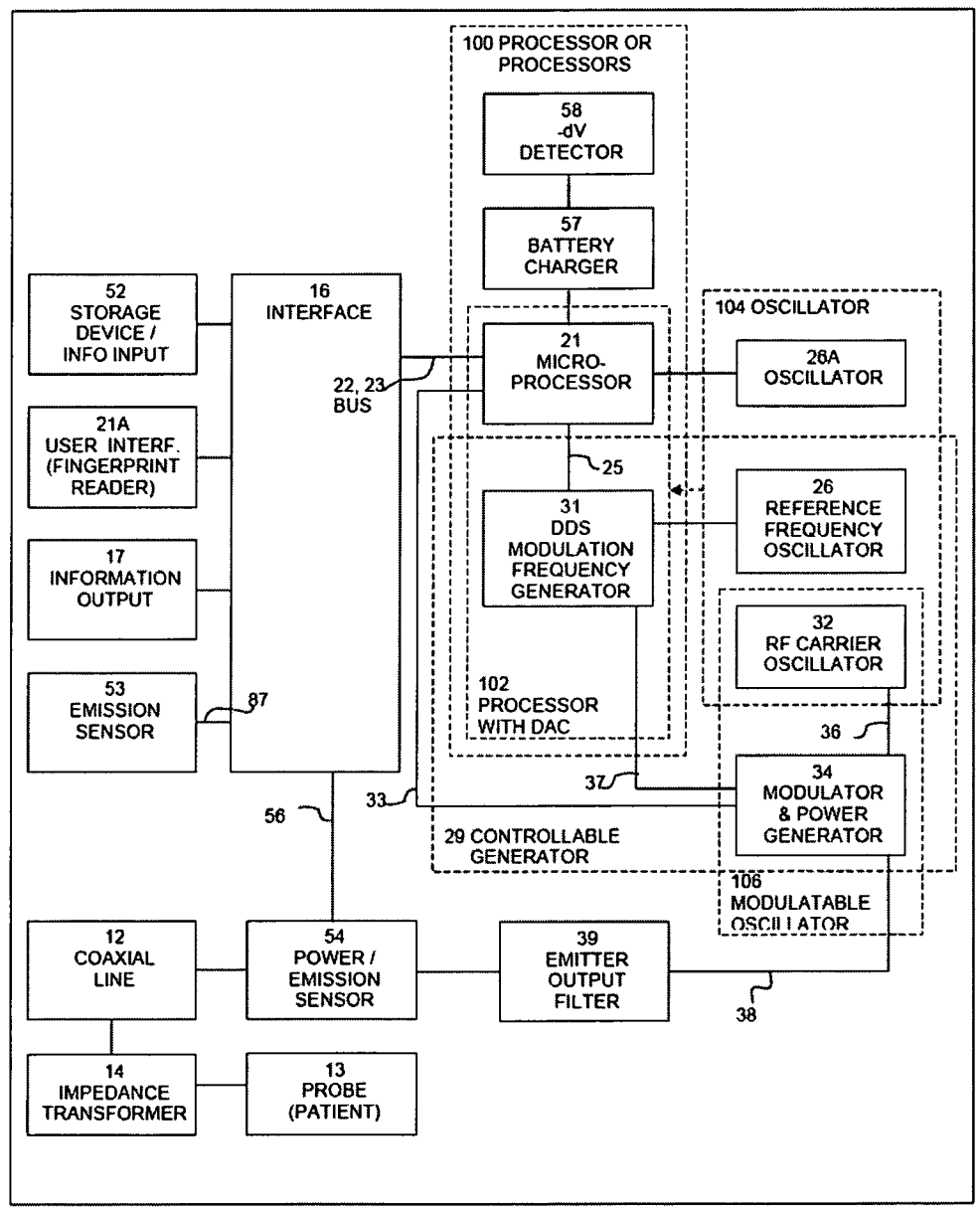

ELECTRONIC SYSTEM FOR INFLUENCING CELLULAR FUNCTIONS IN A WARM-BLOODED MAMMALIAN SUBJECT

RELATED APPLICATION

This application claims the benefit of U.S. patent application Ser. No. 12/450,450 filed Sep. 25, 2009, of which the present application is a continuation-in-part.

FIELD OF INVENTION

This invention relates to an electronic system for influencing cellular functions in a warm-blooded mammalian subject. More particularly, the invention concerns research findings related to how earlier electronic systems may be modified and programmed to achieve both improved and additional therapeutic effects.

BACKGROUND OF INVENTION

Reference is made to European Patent EP 0 592 851 B1 and corresponding patents and patent applications and to the various publications referred to therein. Since the time of the priority application filed in the USA on 25 Sep. 1992 (U.S. Ser. No. 951,563 now U.S. Pat. No. 5,441,528), a number of further publications related to effects of very low energy electromagnetic fields on patients suffering from insomnia and/or anxiety disorders have taken place and are as follows:

Koziol, J. A., Erman, M., Pasche B., Hajdukovic R., Mitler, M. M., (1993), "Assessing a changepoint in a sequence of repeated measurements with application to a low-energy emission therapy sleep study". *J. Applied Statistics* 20: 393-400;

Amato, D., Pasche, B., (1993), "An evaluation of the safety of low energy emission therapy". *Compr Ther* 19: 242-247;

Higgs, L., Reite, M., Barbault, A., Lebet, J. P., Rossel, C., Amato, D., Dafni, U., Pasche. B., (1994), "Subjective and Objective Relaxation Effects of Low Energy Emission Therapy". *Stress Medicine* 10: 5-13;

Reite, M., Higgs, L, Lebet, J. P., Barbault, A., Rossel, C., Kuster, N., Dafni, U., Amato, D., Pasche, B., (1994), "Sleep Inducing Effect of Low Energy Emission Therapy". *Bioelectromagnetics* 15: 67-75.

Lebet, J. P., Barbault, A., Rossel, C., Tomic, Z., Reite, M., Higgs, L., Dafni, U., Amato, D., Pasche, B., (1996), "Electroencephalographic changes following low energy emission therapy". *Ann Biomed Eng* 24: 424-429;

Pasche, B., Erman, M., Hayduk, R., Mitler, M., Reite, M., Higgs, L., Dafni, U., Amato, D., Rossel, C., Kuster, N., Barbault, A., Lebet, J. P., (1996), "Effects of Low Energy Emission Therapy in chronic psychophysiological insomnia". *Sleep* 19: 327-336;

Kelly, T. L., Kripke, D. F., Hayduk, R., Ryman, D., Pasche, B., Barbault, A., (1997), "Bright light and LEET effects on circadian rhythms, sleep and cognitive performance". *Stress Medicine* 13: 251-258; and Pasche, B., Barbault, A., (2003), "Low-Energy Emission Therapy Current Status and Future Directions. In *Bioelectromagnetic Medicine*", Rosch, P. J., Markov, M. S. (eds.), pages 321-327, Marcel Dekker, Inc.: New York, N.Y.

The above publications are related to an earlier device, system and use thereof described in said EP 0 592 851 B1. The improved electronic system and programmed control thereof in accordance with the present invention, however, has been determined to find therapeutic application not only for influencing cellular functions (or malfunctions) leading to central nervous system (CNS) disorders, but more particularly for influencing other cellular functions (or malfunctions) including directly or indirectly influencing cancerous cell growth or proliferation thereof in warm-blooded mammalian subjects. The direct or indirect influence on cancerous cell growth may involve but is not necessarily limited to any of prophylactic avoidance of cancerous cell formation, influencing of cell functions such as for example influencing leukocyte cell functions which can lead to inhibition of cancerous cell growth or proliferation thereof, and/or killing of cancerous cells harboured by a warm-blooded mammalian subject.

Electromagnetic energy generating devices and use of electromagnetic energies for treating living mammalian subjects harbouring cancerous cells described in the literature include: U.S. Pat. No. 5,908,441 issued Jun. 1, 1999 to James E. Bare and the references cited therein and so-called "NovoCure technology" involving in vivo implantation of electrodes to either side of tumorous growths. This literature, however, does not contemplate very low energy emissions of electromagnetic energy involving amplitude-modulated high frequency carrier signals as required in terms of the present invention.

U.S. Pat. No. 5,690,692 issued Nov. 25, 1997 entitled "Bio-Active Frequency Generator and Method" describes a programmable control which instructs a frequency synthesizer to enable generation of an electrical current at a specific precise frequency signal or at a series of specific precise frequency signals having a square wave form to within an accuracy of 0.001 Hz. This patent contemplates amplifying the voltage of the generated signals and applying the signals to a subject at the specific precise frequency or sequentially at the series of specific precise frequencies by means of electrodes held by or otherwise connected to the subject (which may be a mammal or a food). Once again, this patent does not contemplate very low energy emissions involving amplitude-modulated high frequency carrier signals as required in terms of the present invention.

SUMMARY OF THE INVENTION

In one aspect of the invention, an electronic system is provided which is activatable by electrical power. The system is employed to influence cellular functions or malfunctions in a warm-blooded mammalian subject. The system comprises one or more controllable low energy electromagnetic energy generator circuits for generating one or more high frequency radio frequency RF carrier signals. One or more microprocessors or integrated circuits comprising or communicating with the one or more generator circuits are provided which are also for receiving control information from a source of programmed control information. The one or more generator circuits include one or more amplitude modulation control signal generators for controlling amplitude modulated variations of the one or more high frequency carrier signals. The one or more generator circuits furthermore include one or more programmable amplitude modulation frequency control signal generators for controlling the frequency at which the amplitude modulations are generated. The one or more amplitude modulation frequency control generators are, in terms of an important improvement of the present invention, adapted to accurately control the frequency of the amplitude modulations to within an accuracy of at least 1000 parts per million (ppm) relative to one or more determined or predetermined reference amplitude modulation frequencies selected from within a range of 0.01 Hz to 150 kHz. The system furthermore comprises a connection or coupling position for connection or coupling to or being connected or coupled to an electrically conductive applicator for applying to the warm-blooded mammalian subject the one or more amplitude-modulated low energy emissions at said accurately controlled modulation frequencies.

As used herein, the term, "accurately controlled" means that the modulated low energy electromagnetic emissions should be modulated to within a resolution of at most about 1 Hz of intended higher frequencies (greater than about 1000 Hz) determined or predetermined modulation frequencies. For example, if one of the one or more determined or predetermined modulation frequencies to be applied to the warm-blooded mammalian subject is about 2000 Hz, the accurate control should lead to such modulated low energy emission being generated at a frequency of between about 1999 and about 2001 Hz. However, and in terms of what has been determined from experiences in treating human subjects harbouring cancerous cells with the aim of arresting proliferation or killing of such cells, it is preferable that the accurate control should lead to a resolution of about 0.5, more preferably about 0.1, yet more preferably about 0.01 and indeed most preferably about 0.001 Hz of the intended determined or predetermined modulation frequency.

Of importance is the requirement for emissions to be at a very low and safe energy level and result in low levels of absorption, the reason believed to be that physiological exchanges or flow of electrical impulses within warm-blooded animals (which are to be affected by application of the emissions of the present invention) are similarly at very low energy levels. In any event, in the region (at or near to the position of contact or close-by induction of the electrically conductive applicator with a subject receiving treatment), the specific absorption rate (SAR) should be and is most preferably substantially less than 1.6 milliW/g weight of living tissue.

Furthermore of importance to achieve the intended biological therapeutic effect is that the stability of the emissions be maintained during emission, and that such stability should preferably be of the order of $10^{-5}$, more preferably $10^{-6}$, and most preferably $10^{-7}$, stability being determined as the relative deviation of frequency divided by the desired frequency, e.g., 0.01 Hz (deviation)/1,000 Hz (desired freq.)=$10^{-5}$.

As already described in said EP 0 592 851 B1, the system includes a microprocessor (which may more recently be replaced by an integrated circuit) into which control information is loaded from an application storage device. The microprocessor (or now alternatively integrated circuit) then controls the function of the system to produce the desired therapeutic emissions. Also described is the provision in the system of an impedance transformer connected intermediate the emitter of low energy electromagnetic emissions and a probe (here more broadly described as an electrically conductive applicator) for applying the emissions to the patient. The impedance transformer substantially matches the impedance of the patient seen from the emitter circuit with the impedance of the output of the emitter circuit.

BRIEF DESCRIPTION OF THE DRAWINGS

FIG. 2 is a block diagram of exemplary circuitry which may be comprised in the exemplary casing structure of FIG. 1. This FIG. 2 differs essentially from FIG. 2 of EP 0 592 851 B1 by comprising a highly accurate modulation frequency generator 31 (named a Digital Direct Synthesizer or DDS), which enables accurate control of modulatable oscillator represented by dotted line block 106.

Figure 1:
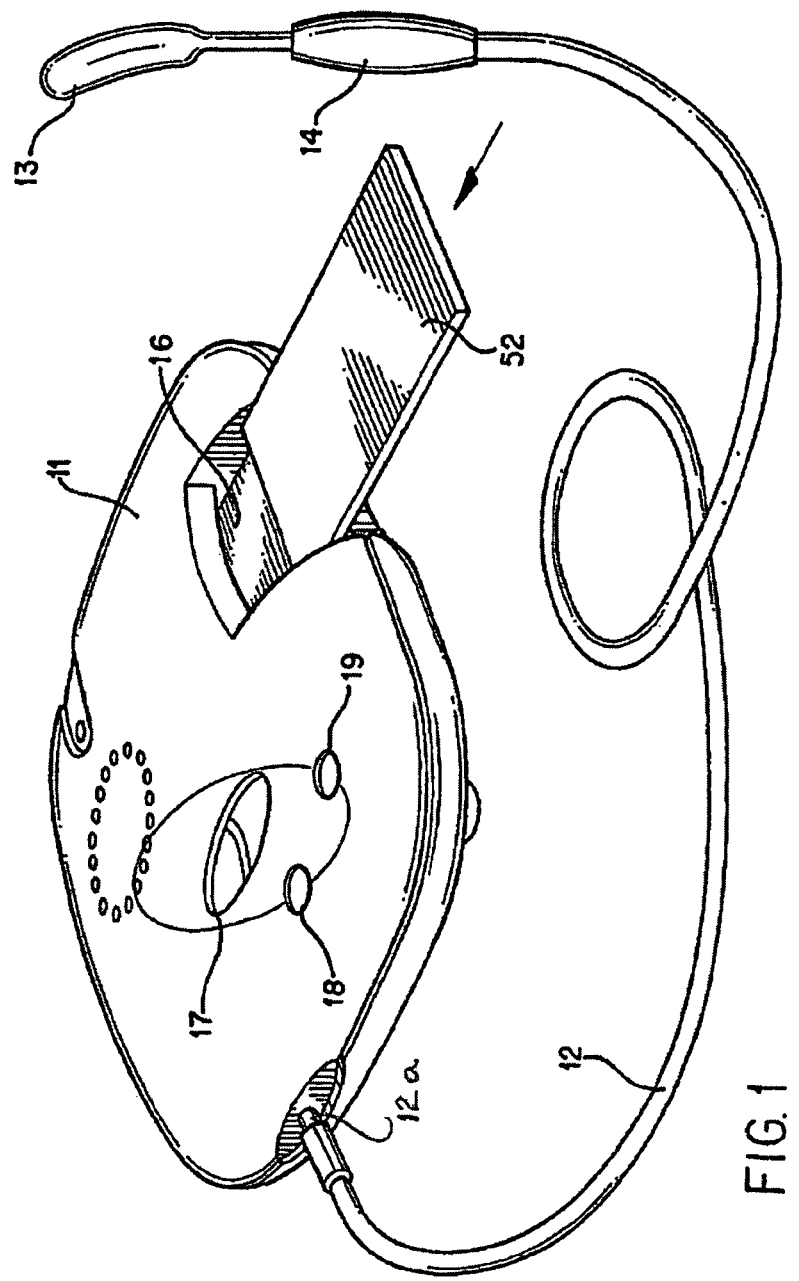
FIG. 1 shows an exemplary casing structure for the electronic circuit shown in FIG. 2, an applicator 13 (exemplified as a probe suitable for being placed in the mouth of a patient) and an interface 16 (which may be replaced by a receiver) for receiving information from a source of information 52 such as may be comprised in an information storage device, e.g., of the nature described and illustrated in FIGS. 12 to 17 of EP 0 592 851 B1.

Reference is made to the various Figures of EP 0 592 851 B1 and the detailed description thereof, a number of which are exemplary of components which may be comprised in the circuit of FIG. 2.

Thus, FIG. 3 of EP 0 592 851 B1 is a detailed schematic of a modulation signal generator 31, replaced by a DDS modulation frequency generator 31 comprised in the circuit of present FIG. 2.

FIG. 4 of EP 0 592 851 B1 is a detailed schematic of a modulation signal buffer and carrier oscillator circuit which may be employed in the circuit of the present FIG. 2.

FIG. 5 of EP 0 592 851 B1 is a detailed schematic example of an amplitude modulation (AM) and power generator 34 and output filter 39 which could be comprised in the circuit of the present FIG. 2.

FIG. 6 of EP 0 592 851 B1 is a detailed schematic example of an impedance transformer 14 which may be comprised in the circuit of the present FIG. 2.

FIG. 7 of EP 0 592 851 B1 is a detailed schematic example of an emission sensor 53 which may be comprised in the circuit of the present FIG. 2.

FIG. 8 of EP 0 592 851 B1 is a detailed schematic example of an output power sensor circuit 54 which may be employed in the circuit of the present FIG. 2.

FIG. 9 of EP 0 592 851 B1 is a detailed schematic example of a display module or information output 17 which may be included in the circuit of the present FIG. 2.

FIG. 10 of EP 0 592 851 B1 is a detailed schematic example of a power supply control circuit including battery charger 57 which may be comprised in the circuit of the present FIG. 2.

FIGS. 11 a-d of EP 0 592 851 B1 are exemplary flow charts of the method of operation of the system of FIGS. 1 and 2.

DETAILED DESCRIPTION OF THE PREFERRED EMBODIMENTS

Referring to FIG. 1, presented is a modulated low energy electromagnetic emission application system 11, in accordance with the present invention. As described in prior U.S. Pat. Nos. 4,649,935 and 4,765,322, such a system has proven to be useful in the practice of Low Energy Emission Therapy (LEET, a trademark of Symtonic S.A. or a successor of this Company), which involves application of emissions of low energy radio frequency (RF) electromagnetic waves to a warm-blooded mammalian subject. The application has proven to be an effective mode of treating a warm-blooded mammalian subject suffering from central nervous system (CNS) disorders such as, for example, generalized anxiety disorders, panic disorders, sleep disorders including insomnia, psychiatric disorders such as depression, obsessive compulsive disorders, disorders resulting from substance abuse, sociopathy, post traumatic stress disorders or other disorders of the central nervous system and combinations thereof.

The system includes an electrically conductive applicator 12, 13 for applying one or more electromagnetic emissions to the warm-blooded mammalian subject. One form of applicator may consist of an electrically conductive probe or mouthpiece 13 which is inserted into the mouth of a subject undergoing treatment. Probe 13 is connected to an electromagnetic energy emitter (see also FIG. 2), through coaxial cable 12 and impedance matching transformer 14.

It has previously been considered that an efficient connection of an electrically conductive applicator to a subject could only be achieved by means of a probe which is adapted to be applied to any mucosa of the subject, such as by being located within oral, nasal, optical, urethral, anal, and/or vaginal cavities or surfaces. It has, however, now been determined that in fact satisfactory application of emissions to a patient can be achieved by simpler physical contact of the electrically conductive applicator with the skin of the patient. Emissions to the patient may, for example be achieved by a conductive, inductive, capacitive or radiated coupling to the patient. An example of a coupling found to be effective involving indirect physical contact with the skin of a patient, is an insulated applicator to be placed over or within an ear of the patient. The emissions thus passed to the patient may be either by capacitive or radiated means or by a combination of both. An important advantage of a device which does not need to be placed in the mouth of a patient is that the patient is able to speak clearly during a time of treatment and can receive treatment during activities of daily living. The treatment is accordingly more user-friendly, can be administered for longer periods of time and can lead to enhanced patient compliance.

Electronic system 11 also includes a connector or coupler for connection to a programmable device such as a computer or an interface or receiver 16 which is adapted to receive an application storage device 52 such as, for example, magnetic media, semiconductor media, optical media or mechanically encoded media, or programmed emissions programmed with control information employed to control the operation of system 11 so that the desired type of low energy emission therapy is applied to the patient.

Application storage device 52 can be provided with a microprocessor which, when applied to interface 16, operates to control the function of system 11 to apply the desired low energy emission therapy. Alternatively, application storage device 52 can be provided with a microprocessor which is used in combination with microprocessor 21 within system 11. In such case, the microprocessor within device 52 could assist in the interfacing of storage device 52 with system 11, or could provide security checking functions.

System 11 may also include a display 17 which can display various indications of the operation of system 11. In addition, system 11 may include on and off power buttons 18 and 19, optionally replaced by user interface 21A (refer to FIG. 2).

Referring to FIG. 2, presented is a block diagram of exemplary electronic circuitry of system 11, in accordance with the present invention. A data processor, such as for example, microprocessor or integrated circuit 21, operates as the controller for electronic system 11, and is connected to control the various components of the system 11, for example, through address bus 22, data bus 23 and input/output lines 25. The block diagram of FIG. 2 is modified as compared to FIG. 2 of EP 0 592 851 B1 by including what is known as a digital direct synthesizer (DDS) 31 which operates as an accurate and stable modulation frequency generator within the system 11. An exemplary DDS device is available from Analog Devices of Norwood, Mass. 02062-9106, USA, Part No. AD9835. The device is a numerically controlled oscillator and modulation capabilities are provided for phase modulation and frequency modulation. As represented by dotted line block 102, entitled "PROCESSOR WITH DAC", the functionality of the DDS may also be combined with microprocessor 21 with digital to analogue converter (DAC).

Microprocessor 21 preferably includes internal storage for the operation of a coded control program, and temporary data. In addition, microprocessor 21 may include input/output ports and internal timers. Microprocessor 21 may be a microcontroller, for example microcontrollers 8048 or 8051 available from Intel Corporation of Santa Clara, Calif. 95054-1549, USA.

The timing for microprocessor 21 is provided by system clock oscillator 26A which may be run at any clock frequency suitable for the particular type of microprocessor used. An exemplary clock frequency is about 8.0 MHz. Oscillator 26A may be replaced by reference frequency oscillator 26 which secures the stability of the accurate modulation frequency. RF (radio frequency) oscillator 32 may also be employed for this purpose. A combination of oscillators is represented by dotted line block 104, entitled "OSCILLATOR".

An exemplary operating program for microprocessor 21 is presented in flow chart form with reference to FIGS. 11 a-d of EP 0 592 851 B1. In general, microprocessor 21 functions to control controllable electromagnetic energy generator circuit 29 to produce a desired form of modulated low energy electromagnetic emission for application to a subject through applicator or probe 13.

Dotted line block 29, entitled CONTROLLABLE GENERATOR, includes DDS modulation frequency generator 31 and carrier signal oscillator 32. Microprocessor 21 operates to activate or de-activate controllable generator circuit 29 through oscillator disable line 33, as described in greater detail in EP 0 592 851 B1. Controllable generator circuit 29 also includes an AM modulator and power generator 34 which operates to amplitude modulate a carrier signal produced by carrier oscillator 32 on carrier signal line 36, with a modulation signal produced by modulation signal generator circuit 31 on modulation signal line 37. The combination of the functionality of the DDS modulation frequency generator 31, with processor 21 with DAC, represented by dotted line block 102, enables output lines 33 and 37 to be combined to produce a single signal. The combination furthermore enables arbitrary or periodic wave forms of any shape to be generated, as similarly described in EP 0 592 851 B1.

AM modulator and power generator 34 produces an amplitude modulated carrier signal on modulated carrier signal line 38, which is then applied to emitter output filter circuit 39. The filter circuit 39 is connected to probe or applicator 13 via power emission sensor 54, coaxial cable 12 and impedance transformer 14.

Microprocessor 21 controls DDS modulation signal generator circuit 31 of controllable generator circuit 29 via interface lines 25.

As is illustrated and described in EP 0 592 851 B1, microprocessor 21 may select a desired waveform stored in a modulation waveform storage device 43 and also controls a waveform address generator 41 to produce on waveform address bus 42 a sequence of addresses which are applied to modulation signal storage device 43 in order to retrieve the selected modulation signal. In the embodiment described in EP 0 592 851 B1, the desired modulation signal is retrieved from modulation signal storage device 43 and applied to modulation signal bus 44 in digital form. Modulation signal bus 44 is applied to wave form generator and DAC 46 which converts the digital modulation signal into analogue form. This analogue modulation signal is then applied to a selective filter 47 which, under control of microprocessor 21, filters the analogue modulation signal by use of a variable filter network including resistor 48 and capacitors 49 and 51 in order to smooth the wave form produced by DAC 46 on modulation signal line 20.

A further embodiment possibility is a combination of PROCESSOR WITH DAC dotted line block 102 with OSCILLA- TOR dotted line block 104 or with a combination of oscillators 26 and 26A. With such a combination, the hardware solution described in EP 0 592 851 B1 can be realized internally in the processor 102 with multiple outputs 33 and 37 or a single output combining these signals.

The above embodiment from EP 0 592 851 B1 is in part replaced by the functionality of the DDS modulation frequency modulator 31. However, if it is determined that emissions of different wave forms is, desirable, it would be desirable to include the modulation signal storage device 43 and wave form generator 46 described in EP 0 592 851 B1. Various modulation signal wave forms may then be stored in modulation signal storage device 43. Wave forms that have been successfully employed include square wave forms or sinusoidal wave forms. Other possible modulation signal wave forms include rectified sinusoidal, triangular, or other wave forms and combinations of all of the above.

The particular modulation control information employed by microprocessor 21 to control the operation of controllable generator circuit 29, is stored in application storage device 52. The application storage device is conveniently a computer comprising or being for receiving the information. Alternatively, application storage devices illustrated and described in EP 0 592 851 B1, with reference to FIGS. 12, 13, 14 and 15, may be selected.

Interface 16 is configured as appropriate for the particular application storage device 52 in use. Interface 16 translates the control information stored in application storage device 52 into a usable form for storage within the memory of microprocessor 21 to enable microprocessor 21 to control controllable generator circuit 29 to produce the desired modulated low energy emission.

Interface 16 may directly read the information stored on application storage device 52, or it may read the information through use of various known communication links. For example, radio frequency, microwave, laser, telephone, internet or optical based communications links may be employed to transfer information between interface or receiver 16 and application storage device or computer 52.

The system 11 may comprise a user identification device, included in block 21a in FIG. 2. Conveniently, such a device communicates with the one or more data processors or integrated circuits 21 via interface 16, as shown. The user identification device may be of any type, a finger print reader being an example. Such a reader is for example available from Lenovo, 70563 Stuttgart, Germany, Part No. 73P4774.

The control information stored in application storage device or computer 52 specifies various controllable parameters of the modulated low energy RF electromagnetic emission to be applied to a subject through applicator or probe 13. Such controllable parameters include, for example, but are not necessarily limited to, the frequency and amplitude of the carrier, the amplitudes and frequencies and wave forms of the modulation of the carrier, the duration of the emission, the power level of the emission, the duty cycle of the emission (i.e., the ratio of on time to off time of pulsed emissions applied during a treatment), the sequence of application of different modulation frequencies for a particular application, and the total number of treatments and duration of each treatment prescribed for a particular subject, and combinations thereof.

For example, the carrier signal and modulation signal may be selected to drive the applicator or probe 13 with an amplitude modulated signal in which the carrier signal includes spectral frequency components below about 1 GHz, and preferably between about 1 MHz and about 900 MHz, and in which the modulation signal comprises spectral frequency components between about 0.01 Hz and 150 KHz. The one or more modulation frequencies may be simultaneously emitted or sequenced to form the modulation signal.

As an additional feature, an electromagnetic emission sensor 53 may be provided to detect the presence of electromagnetic emissions at the frequency of the carrier oscillator 32. Emission sensor 53 provides microprocessor 21 with an indication of whether or not electromagnetic emissions at the desired frequency are present. Microprocessor 21 then takes appropriate action, for example, by displaying an error message on display 17, disabling controllable generator circuit 29, or the like.

A power sensor 54 is preferably included which detects the amount of power applied to the subject through applicator or probe 13 compared to the amount of power returned or reflected from the subject. This ratio is indicative of the proper use of the system during a therapeutic session. Power sensor 54 applies to microprocessor 21, through power sensor line 56, an indication of the amount of power applied to patient through applicator or probe 13 relative to the amount of power reflected from the patient.

The indication provided on power sense line 56 may be digitalized and employed by microprocessor 21, for example, to detect and control a level of applied power, and to record on application storage device 52 information related to the actual treatments applied to and received by the patient. Such information may then be used by a physician or other clinician to assess patient treatment compliance and effect. Such treatment information may include, for example: the number of treatments applied for a given time period; the actual time and date of each treatment; the number of attempted treatments; the treatment compliance (i.e., whether the applicator or probe was in place or not during the treatment session); and the cumulative dose of a particular modulation frequency.

The level of power applied is preferably controlled to cause the specific absorption rate (SAR) of energy absorbed by the patient to be from about 1 microWatt per kilogram of tissue to about 50 Watts per kilogram of tissue. Preferably, the power level is controlled to cause an SAR of from about 100 microWatts per kilogram of tissue to about 10 Watts per kilogram of tissue. Most preferably, the power level is controlled to cause an SAR of from about 1 milliWatt per kilogram of tissue to about 100 milliWatts per kilogram of tissue. These SARs may be in any tissue of the patient, but are preferably in the tissue of the central nervous system or the diseased tissue.

System 11 may also include powering circuitry including battery and charger circuit 57 and battery voltage change detector 58.

The RF carrier oscillator 32 produces a RF carrier frequency of about 27 MHz. Other embodiments of the invention contemplate RF carrier frequencies of about 48 MHz, about 433 MHz or about 900 MHz. In general, the RF carrier frequency produced by carrier oscillator 32 has spectral frequency components less than about 1 GHz and preferably between about 1 MHz and about 916 MHz. Although the described embodiment contemplates that once set, the carrier oscillator frequency remains substantially constant, the carrier frequency produced by carrier oscillator 32 may be variable and controllable by microprocessor 21 by use of stored or transmitted control information.

Carrier oscillator 32 produces on carrier signal line 36 a carrier signal which is then modulated by the modulation signal carried on signal line 37.

Oscillator disable line 33 enables microprocessor 21 to disable the signal from oscillator 32 by applying an appropriate disable signal to oscillator disable line 33.

The output of the AM modulator and power generator 34 appears on signal line 38. This modulated signal is applied through emitter output filter 39 which substantially reduces or eliminates the carrier harmonics resulting from side effects of the modulator and power generator circuit 34.

The output of the AM modulator and power generator 34 and emitter output filter 39 may be designed to possess a 50 Ohm output impedance to match a 50 Ohm impedance of coaxial cable 12.

It has been determined through impedance measurements that when a probe 13 is applied within the mouth of a subject, the probe/subject combination exhibits a complex impedance of the order of about 150+j200 Ohms. Impedance transformer 14 serves to match this complex impedance with the 50 Ohm impedance of coaxial cable 12 and therefore the output impedance of the AM modulator 34 and output filter 39. This promotes power transmission, and minimizes reflections.

The arrangement described above has been optimized for a contact probe with coupling to the mucosa of the mouth. In a further example, a conductive, isolated probe has been used at a frequency around 433 MHz coupling to the outer ear channel. Due to the different probe design in such a frequency band and with this coupling method, the values of matching elements (79 and 81 described in EP 0 592 851 B1) would be different or could even be omitted. Applicator or probe 13 may then be regarded as a capacitive coupler or as an antenna matched to the capacitive load.

As described in EP 0 592 851 B1, with reference to the flow charts of FIGS. 11 a-d, microprocessor 21 may operate to analyze the signal appearing on power sense line 56 to determine and control the amount of power applied to the patient, and to assess patient treatment compliance, and possibly to record indicia of the patient treatment compliance on application storage device 52 for later analysis and assessment by a physician or other clinician.

Exemplary of treatments performed on patients have included brain, bladder, colorectal, kidney, mesothelium, neuroendocrine, liver, lung, breast, ovary, pancreas, prostate and thyroid tumor types. The treatments involved applying an about 27.12 MHz RF signal, amplitude modulated at specifically defined frequencies ranging from about 0.2 to about 23,000 Hz at very high precision and stability. Further Examples of treatment modes (at specific accurately controlled AM frequencies) for specified types of tumors are described in detail below.

The following are synopses of abstracts for future publications related to uses of electronic devices of the present invention:

Example A

A Phase I Study of Therapeutic Amplitude-Modulated Electromagnetic Fields (THERABIONIC) in Advanced Tumors Boris Pasche [1], Alexandre Barbault [1], Brad Bottger [2], Fin Bomholt [3], Niels Kuster [4].
[1] Cabinet Médical de l'Avenue de la Gare 6, CH-1003-Lausanne, Switzerland.
[2] Danbury Hospital, Danbury, CT-06810.
[3] SPEAG, Zurich, CH-8004-Zurich, Switzerland.
[4] IT'IS Foundation, Swiss Federal Institute of Technology, Zurich, Switzerland.
Background:

In vitro studies suggest that low levels of amplitude-modulated electromagnetic fields may modify cell growth. Specific frequencies have been identified specific frequencies that may block cancer cell growth. A portable and programmable device capable of delivering low levels of amplitude-modulated electromagnetic fields has been developed. The device emits a 27.12 MHz radiofrequency signal, amplitude-modulated at cancer-specific frequencies ranging from 0.2 to 23,000 Hz with high precision. The device is connected to a spoon-like coupler, which is placed in the patient's mouth during treatment.

Methods:

A phase I study was conducted consisting of three daily 40 min treatments. From March 2004 to September 2006, 24 patients with advanced solid tumors were enrolled. The median age was 57.0±12.2 years. 16 patients were female. As of January 2007, 5 patients are still on therapy, 13 patients died of tumor progression, 2 patients are lost to follow-up and one patient withdrew consent. The most common tumor types were breast (7), ovary (5) and pancreas (3). 22 patients had received prior systemic therapy and 16 had documented tumor progression prior to study entry.

Results:

The median duration of therapy was 15.7±19.9 weeks (range: 0.4-72.0 weeks). There were no NCI grade 2, 3 or 4 toxicities. Three patients experienced grade 1 fatigue during and immediately after treatment. 12 patients reported severe pain prior to study entry. Two of them reported significant pain relief with the treatment. Objective response could be assessed in 13 patients, 6 of whom also had elevated tumor markers. 6 additional patients could only be assessed by tumor markers. Among patients with progressive disease at study entry, one had a partial response for >14.4 weeks associated with >50% decrease in CEA, CA 125 and CA 15-3 (previously untreated metastatic breast cancer); one patient had stable disease for 34.6 weeks (add info); one patient had a 50% decrease in CA 19-9 for 12.4 weeks (recurrent pancreatic cancer). Among patients with stable disease at enrollment, four patients maintained stable disease for 17.0, >19.4, 30.4 and >63.4 weeks.

Conclusions:

The treatment is a safe and promising novel treatment modality for advanced cancer. A phase II study and molecular studies are ongoing to confirm those results.

Example B

A Phase II Study of Therapeutic Amplitude-Modulated Electromagnetic Fields (THERABIONIC) in the Treatment of Advanced Hepatocellular Carcinoma (HCC)

Frederico P Costa [1], Andre Cosme de Oliveira [1], Roberto Meirelles Jr [1], Rodrigo Surjan [1], Tatiana Zanesco [1], Maria Cristina Chammas [1], Alexandre Barbault [2], Boris Pasche [2].
[1] Hospital das Clínicas da Faculdade de Medicina da Universidade de São Paulo, São Paulo, Brazil. [2] Cabinet Médical Avenue de la Gare 6, CH-1003-Lausanne, Switzerland.
Background:

Phase I data suggest that low levels of electromagnetic fields amplitude-modulated at specific frequencies administered intrabucally with the device of Example A are a safe and potentially effective treatment for advanced cancer. The device emits a 27.12 MHz RF signal, amplitude-modulated with cancer-specific frequencies ranging from 0.2 to 23,000 Hz with high precision. The device is connected to a spoon-like coupler placed in the patient's mouth during treatment. Patients with advanced hepatocellular carcinoma HCC and limited therapeutic options were offered treatment with a combination of HCC-specific frequencies.

Methods:

From October 2005 to October 2006, 38 patients with advanced HCC were recruited in a phase II study. The patients received three daily 40 min treatments until disease progression or death. The median age was 64.0±14.2 years. 32 patients were male and 29 patients had documented progression of disease (POD) prior to study entry.

Results:

As of January 2007, 12 patients are still on therapy, 20 patients died of tumor progression, 2 patients are lost to follow-up and 3 patients withdrew consent. 27 patients are eligible for response. The overall objective response rate as defined by partial response (PR) or stable disease (SD) in patients with documented POD at study entry was 31.6%: 3 PR and 9 SD. The median survival was 20.7 weeks with a median duration of therapy of 17.5 weeks. 13 patients have received therapy for more than six months. The median duration of response is 12.9 weeks. 12 patients reported pain at study entry: 8 of them (66%) experienced decreased pain during treatment. There were no NCI grade 2/3/4 toxicities. One patient developed grade 1 mucositis and grade 1 fatigue.

| Patient characteristics (n = 38) | | | |
|---|---|---|---|
| Cirrhosis | | 36 | |
| Portal vein thrombosis | | 9 | |
| Elevated AFP | | 25 | |
| Extra-hepatic metastases | | 12 | |
| Previous intrahepatic/systemic therapy | | 30 | |
| Previous hepatic resection/RFA or ethanol | | 8 | |
| CLIP | 0/1: | 12 | ≥2: 22 |
| Okuda | I: | 14 | II/III: 20 |
| Child-Pugh | A: | 15 | B: 19 |
| MELD | Median: | 10 | |

Conclusion:

In patients with advanced HCC the treatment is a safe and effective novel therapeutic option, which has antitumor effect and provides pain relief in the majority of patients.

Thus, it seen that the electronic device of the present invention, comprising means for the accurate control over the frequencies and stability of amplitude modulations of a high frequency carrier signal, provides a safe and promising novel treatment modality for the treatment of patients suffering from various types of advanced forms of cancer.

Exemplary of above accurately controlled amplitude modulated frequencies controlling the frequency of amplitude modulations of a high frequency carrier signal are set forth below along with the type of cancer or tumor harbored by a subject to be treated.

Example 1

AM Frequencies Employed for Treatment of Breast Cancer (232 Frequencies so Far Included)

78.76 Hz
181.821 Hz
331.3 Hz
414.817 Hz
430.439 Hz
440.933 Hz
618.8 Hz
628.431 Hz
655.435 Hz
677.972 Hz
721.313 Hz
752.933 Hz
813.205 Hz
818.342 Hz
825.145 Hz
839.521 Hz
841.211 Hz
843.312 Hz
891.901 Hz
929.095 Hz
929.1 Hz
929.131 Hz
958.929 Hz
1021 Hz
1021.311 Hz
1156.79 Hz
1372.207 Hz
1372.934 Hz
1555.282 Hz
1588.721 Hz
1624.802 Hz
1670.699 Hz
1821.729 Hz
1836.219 Hz
2193.937 Hz
2221.323 Hz
2278.312 Hz
2332.949 Hz
2357.832 Hz
2381.443 Hz
2417.323 Hz
2423.292 Hz
2431.334 Hz
2450.332 Hz
2551.313 Hz
2556.221 Hz
2598.853 Hz
2621.322 Hz
2740.191 Hz
2823.428 Hz
2831.386 Hz
2851.347 Hz
2885.322 Hz
2919.273 Hz
3074.333 Hz
3115.188 Hz
3239.212 Hz
3249.529 Hz
3405.182 Hz
3432.274 Hz
3434.693 Hz
3594.231 Hz
3647.619 Hz
3657.931 Hz
3742.957 Hz
3753.382 Hz
3830.732 Hz
3855.823 Hz
3916.321 Hz
3935.218 Hz
3975.383 Hz
3993.437 Hz
4153.192 Hz
4194.968 Hz
4241.321 Hz
4243.393 Hz
4253.432 Hz
4314.444 Hz
4318.222 Hz
4375.962 Hz
4393.419 Hz
4394.134 Hz
4417.243 Hz
4481.463 Hz
4482.223 Hz
4495.138 Hz
4549.808 Hz
4558.306 Hz
4751.908 Hz

-continued

| |
|---|
| 4779.451 Hz |
| 4838.674 Hz |
| 4871.513 Hz |
| 4878.687 Hz |
| 4895.296 Hz |
| 4962.213 Hz |
| 4969.224 Hz |
| 4979.321 Hz |
| 5027.231 Hz |
| 5059.792 Hz |
| 5118.094 Hz |
| 5176.287 Hz |
| 5365.222 Hz |
| 5376.392 Hz |
| 5426.323 Hz |
| 5431.542 Hz |
| 5521.621 Hz |
| 5536.242 Hz |
| 5739.422 Hz |
| 5745.218 Hz |
| 5821.975 Hz |
| 6037.432 Hz |
| 6044.333 Hz |
| 6086.256 Hz |
| 6208.932 Hz |
| 6212.808 Hz |
| 6231.031 Hz |
| 6280.321 Hz |
| 6329.391 Hz |
| 6476.896 Hz |
| 6477.098 Hz |
| 6497.319 Hz |
| 6504.983 Hz |
| 6651.276 Hz |
| 6657.913 Hz |
| 6757.901 Hz |
| 6758.321 Hz |
| 6855.286 Hz |
| 6858.121 Hz |
| 6898.489 Hz |
| 6915.886 Hz |
| 7092.219 Hz |
| 7120.218 Hz |
| 7127.311 Hz |
| 7156.489 Hz |
| 7208.821 Hz |
| 7224.197 Hz |
| 7282.169 Hz |
| 7285.693 Hz |
| 7376.329 Hz |
| 7488.742 Hz |
| 7541.319 Hz |
| 7577.421 Hz |
| 7621.085 Hz |
| 7627.207 Hz |
| 7650.939 Hz |
| 7668.231 Hz |
| 7691.212 Hz |
| 7842.184 Hz |
| 7849.231 Hz |
| 7915.423 Hz |
| 7932.482 Hz |
| 7949.196 Hz |
| 7967.311 Hz |
| 8021.229 Hz |
| 8070.181 Hz |
| 8114.032 Hz |
| 8149.922 Hz |
| 8194.19 Hz |
| 8245.801 Hz |
| 8328.322 Hz |
| 8330.534 Hz |
| 8355.987 Hz |
| 8408.121 Hz |
| 8431.184 Hz |
| 8452.119 Hz |
| 8548.324 Hz |
| 8749.383 Hz |
| 8782.421 Hz |

-continued

| |
|---|
| 8784.424 Hz |
| 8887.182 Hz |
| 8894.222 Hz |
| 8923.1 Hz |
| 8923.361 Hz |
| 8935.752 Hz |
| 8936.1 Hz |
| 9012.282 Hz |
| 9012.896 Hz |
| 9060.323 Hz |
| 9072.409 Hz |
| 9131.419 Hz |
| 9199.232 Hz |
| 9245.927 Hz |
| 9270.322 Hz |
| 9279.193 Hz |
| 9393.946 Hz |
| 10227.242 Hz |
| 10340.509 Hz |
| 10363.313 Hz |
| 10449.323 Hz |
| 10456.383 Hz |
| 10468.231 Hz |
| 10470.456 Hz |
| 10472.291 Hz |
| 10689.339 Hz |
| 10832.222 Hz |
| 11525.121 Hz |
| 11541.915 Hz |
| 11812.328 Hz |
| 11812.419 Hz |
| 11840.323 Hz |
| 11925.089 Hz |
| 12123.281 Hz |
| 12267.281 Hz |
| 12294.283 Hz |
| 12334.419 Hz |
| 12611.288 Hz |
| 12629.222 Hz |
| 12633.372 Hz |
| 12648.221 Hz |
| 13315.335 Hz |
| 13331.358 Hz |
| 13735.241 Hz |
| 13826.325 Hz |
| 13853.232 Hz |
| 13915.231 Hz |
| 13990.123 Hz |
| 14122.942 Hz |
| 14162.332 Hz |
| 14519.232 Hz |
| 14543.128 Hz |
| 15651.323 Hz |
| 17352.085 Hz |
| 17970.122 Hz |
| 18524.419 Hz |
| 18619.331 Hz |
| 18662.112 Hz |
| 18679.492 Hz |
| 18785.463 Hz |
| 19385.893 Hz |
| 19406.211 Hz |
| 22479.333 Hz |
| 30182.932 Hz |

Example 2

AM Frequencies Employed for Treatment of Hepatocellular Carcinoma (Liver) Cancer (253 Frequencies so Far Included)

| |
|---|
| 380.293 Hz |
| 410.231 Hz |
| 423.321 Hz |

-continued

| | |
|---|---|
| 427.062 Hz | 3669.513 Hz |
| 434.332 Hz | 3923.221 Hz |
| 470.181 Hz | 3927.331 Hz |
| 560.32 Hz | 4013.932 Hz |
| 642.932 Hz | 4071.121 Hz |
| 655.435 Hz | 4079.951 Hz |
| 657.394 Hz | 4123.953 Hz |
| 668.209 Hz | 4161.889 Hz |
| 677.972 Hz | 4222.821 Hz |
| 728.232 Hz | 4238.402 Hz |
| 806.021 Hz | 4256.321 Hz |
| 811.924 Hz | 4289.296 Hz |
| 842.311 Hz | 4312.947 Hz |
| 843.22 Hz | 4375.962 Hz |
| 845.208 Hz | 4426.387 Hz |
| 891.901 Hz | 4428.185 Hz |
| 914.219 Hz | 4435.219 Hz |
| 920.321 Hz | 4471.188 Hz |
| 964.394 Hz | 4483.889 Hz |
| 1250.504 Hz | 4486.384 Hz |
| 1755.402 Hz | 4556.322 Hz |
| 1814.223 Hz | 4629.941 Hz |
| 1851.202 Hz | 4715.222 Hz |
| 1873.477 Hz | 4732.211 Hz |
| 1924.702 Hz | 4767.185 Hz |
| 1975.196 Hz | 4873.333 Hz |
| 2017.962 Hz | 4876.218 Hz |
| 2053.396 Hz | 5086.281 Hz |
| 2083.419 Hz | 5124.084 Hz |
| 2190.731 Hz | 5133.121 Hz |
| 2221.323 Hz | 5247.142 Hz |
| 2308.294 Hz | 5270.834 Hz |
| 2315.208 Hz | 5340.497 Hz |
| 2324.393 Hz | 5520.218 Hz |
| 2338.221 Hz | 5570.234 Hz |
| 2353.478 Hz | 5882.292 Hz |
| 2362.309 Hz | 5926.512 Hz |
| 2379.571 Hz | 6037.311 Hz |
| 2419.309 Hz | 6180.334 Hz |
| 2425.222 Hz | 6329.195 Hz |
| 2430.219 Hz | 6350.333 Hz |
| 2431.094 Hz | 6361.321 Hz |
| 2471.328 Hz | 6364.928 Hz |
| 2478.331 Hz | 6383.321 Hz |
| 2480.191 Hz | 6461.175 Hz |
| 2522.328 Hz | 6661.109 Hz |
| 2743.995 Hz | 6711.392 Hz |
| 2744.211 Hz | 6733.331 Hz |
| 2831.951 Hz | 6758.232 Hz |
| 2843.283 Hz | 6779.482 Hz |
| 2859.891 Hz | 6856.222 Hz |
| 2873.542 Hz | 6877.183 Hz |
| 2886.232 Hz | 6915.886 Hz |
| 3009.332 Hz | 6980.525 Hz |
| 3020.286 Hz | 7019.235 Hz |
| 3042.012 Hz | 7041.321 Hz |
| 3044.213 Hz | 7043.209 Hz |
| 3051.218 Hz | 7078.307 Hz |
| 3076.892 Hz | 7130.323 Hz |
| 3078.983 Hz | 7144.142 Hz |
| 3086.443 Hz | 7210.223 Hz |
| 3104.854 Hz | 7232.343 Hz |
| 3127.232 Hz | 7291.21 Hz |
| 3160.942 Hz | 7482.245 Hz |
| 3161.331 Hz | 7510.92 Hz |
| 3167.22 Hz | 7529.233 Hz |
| 3206.315 Hz | 7549.212 Hz |
| 3255.219 Hz | 7650.028 Hz |
| 3267.433 Hz | 7680.518 Hz |
| 3269.321 Hz | 7692.522 Hz |
| 3281.432 Hz | 7829.231 Hz |
| 3457.291 Hz | 7862.209 Hz |
| 3505.229 Hz | 7932.482 Hz |
| 3516.296 Hz | 7935.423 Hz |
| 3530.188 Hz | 7947.392 Hz |
| 3531.296 Hz | 7979.308 Hz |
| 3546.323 Hz | 8025.322 Hz |
| 3572.106 Hz | 8028.339 Hz |
| 3576.189 Hz | 8055.942 Hz |

-continued 8072.134 Hz
8141.174 Hz
8208.285 Hz
8328.312 Hz
8336.383 Hz
8394.793 Hz
8432.181 Hz
8452.119 Hz
8460.944 Hz
8475.221 Hz
8492.193 Hz
8542.311 Hz
8779.229 Hz
8818.104 Hz
8852.329 Hz
8853.444 Hz
8858.179 Hz
8915.221 Hz
8939.212 Hz
8953.231 Hz
8993.239 Hz
9278.889 Hz
9332.397 Hz
9381.221 Hz
9520.333 Hz
9719.314 Hz
9740.219 Hz
9768.331 Hz
9773.111 Hz
9797.294 Hz
9819.511 Hz
9845.319 Hz
10015.419 Hz
10043.293 Hz
10317.499 Hz
10438.495 Hz
10443.311 Hz
10456.383 Hz
10579.425 Hz
10863.209 Hz
10866.382 Hz
11067.418 Hz
11149.935 Hz
11163.895 Hz
11195.509 Hz
11421.219 Hz
11802.821 Hz
11953.424 Hz
12024.502 Hz
12223.329 Hz
12228.369 Hz
12247.233 Hz
12260.933 Hz
12265.295 Hz
12267.233 Hz
12267.296 Hz
12274.219 Hz
12623.191 Hz
12633.372 Hz
12685.231 Hz
12721.423 Hz
12785.342 Hz
13433.323 Hz
13457.388 Hz
14085.222 Hz
14212.122 Hz
14226.313 Hz
14333.209 Hz
14537.331 Hz
14542.432 Hz
14655.03 Hz
14736.223 Hz
14828.234 Hz
15149.213 Hz
15237.489 Hz
15560.908 Hz
15717.221 Hz
16110.932 Hz
16144.343 Hz -continued 17153.322 Hz
17660.109 Hz
18121.184 Hz
18265.238 Hz
18283.323 Hz
18863.292 Hz
18930.995 Hz
19970.311 Hz
20330.294 Hz
20365.284 Hz
22321.331 Hz
24119.295 Hz
24181.221 Hz Example 3

AM Frequencies Employed for Treatment of Ovarian Cancer (371 Frequencies so Far Included)

78.76 Hz
181.821 Hz
367.211 Hz
403.218 Hz
410.245 Hz
414.817 Hz
436.332 Hz
447.942 Hz
481.191 Hz
489.292 Hz
537.914 Hz
559.292 Hz
608.321 Hz
618.407 Hz
621.321 Hz
655.435 Hz
657.394 Hz
657.397 Hz
657.483 Hz
664.211 Hz
694.689 Hz
708.787 Hz
708.8 Hz
708.821 Hz
708.822 Hz
734.921 Hz
749.221 Hz
764.232 Hz
778.295 Hz
779.403 Hz
806.021 Hz
806.389 Hz
809.313 Hz
824.327 Hz
825.145 Hz
835.129 Hz
839.521 Hz
841.208 Hz
843.312 Hz
925.309 Hz
956.984 Hz
958.929 Hz
985.313 Hz
1024.208 Hz
1102.635 Hz
1121.329 Hz
1159.738 Hz
1221.321 Hz
1372.207 Hz
1396.498 Hz
1502.181 Hz
1518.208 Hz
1552.123 Hz
1579.212 Hz
1624.802 Hz
1656.431 Hz
1670.699 Hz
1679.432 Hz
1696.403 Hz

-continued 1759.318 Hz
1762.938 Hz
1771.402 Hz
1775.313 Hz
1821.729 Hz
1990.482 Hz
2016.323 Hz
2031.448 Hz
2034.231 Hz
2050.282 Hz
2053.396 Hz
2082.234 Hz
2089.092 Hz
2221.323 Hz
2228.832 Hz
2229.515 Hz
2253.704 Hz
2254.329 Hz
2278.312 Hz
2332.949 Hz
2348.233 Hz
2381.443 Hz
2413.193 Hz
2415.243 Hz
2425.222 Hz
2433.321 Hz
2439.253 Hz
2465.23 Hz
2477.919 Hz
2669.177 Hz
2715.232 Hz
2733.843 Hz
2771.211 Hz
2802.339 Hz
2812.321 Hz
2831.386 Hz
2835.332 Hz
2851.347 Hz
2856.253 Hz
2873.542 Hz
2877.192 Hz
2885.322 Hz
2887.385 Hz
2894.972 Hz
2973.771 Hz
3080.592 Hz
3157.483 Hz
3160.321 Hz
3161.465 Hz
3185.129 Hz
3223.232 Hz
3238.148 Hz
3240.111 Hz
3249.529 Hz
3254.122 Hz
3262.145 Hz
3264.241 Hz
3265.121 Hz
3282.235 Hz
3283.392 Hz
3296.431 Hz
3314.321 Hz
3361.671 Hz
3366.311 Hz
3459.408 Hz
3461.322 Hz
3523.215 Hz
3527.233 Hz
3542.213 Hz
3590.376 Hz
3629.232 Hz
3632.793 Hz
3636.289 Hz
3637.085 Hz
3669.513 Hz
3770.189 Hz
3858.916 Hz
3872.321 Hz
3919.232 Hz -continued 3941.739 Hz
3957.185 Hz
3975.228 Hz
3975.383 Hz
4061.131 Hz
4072.322 Hz
4139.322 Hz
4169.451 Hz
4174.259 Hz
4241.321 Hz
4243.393 Hz
4261.228 Hz
4279.113 Hz
4309.335 Hz
4314.188 Hz
4318.222 Hz
4328.928 Hz
4340.833 Hz
4380.321 Hz
4394.134 Hz
4412.252 Hz
4424.236 Hz
4439.341 Hz
4442.161 Hz
4447.221 Hz
4458.339 Hz
4556.322 Hz
4566.009 Hz
4579.981 Hz
4682.643 Hz
4718.331 Hz
4749.302 Hz
4765.331 Hz
4779.194 Hz
4912.923 Hz
4917.202 Hz
5011.325 Hz
5149.331 Hz
5228.172 Hz
5237.132 Hz
5313.353 Hz
5745.218 Hz
5757.897 Hz
5762.386 Hz
5812.322 Hz
5869.321 Hz
5882.292 Hz
5921.249 Hz
5991.932 Hz
6069.458 Hz
6071.319 Hz
6083.214 Hz
6111.819 Hz
6161.782 Hz
6169.341 Hz
6275.232 Hz
6294.929 Hz
6350.333 Hz
6356.321 Hz
6406.891 Hz
6407.207 Hz
6450.787 Hz
6477.098 Hz
6477.929 Hz
6478.338 Hz
6504.983 Hz
6543.421 Hz
6552.24 Hz
6661.09 Hz
6663.955 Hz
6753.338 Hz
6789.211 Hz
6851.323 Hz
6855.286 Hz
6875.232 Hz
6882.949 Hz
7047.223 Hz
7206.403 Hz
7232.214 Hz 7257.489 Hz
7276.209 Hz
7279.335 Hz
7281.219 Hz
7285.223 Hz
7285.693 Hz
7289.192 Hz
7326.229 Hz
7399.223 Hz
7429.212 Hz
7460.932 Hz
7480.228 Hz
7488.742 Hz
7495.763 Hz
7539.432 Hz
7564.185 Hz
7650.028 Hz
7689.728 Hz
7780.294 Hz
8021.921 Hz
8038.961 Hz
8040.322 Hz
8044.233 Hz
8054.413 Hz
8095.313 Hz
8141.174 Hz
8143.491 Hz
8164.332 Hz
8261.121 Hz
8302.285 Hz
8309.752 Hz
8372.532 Hz
8408.121 Hz
8424.229 Hz
8428.313 Hz
8430.142 Hz
8435.451 Hz
8486.421 Hz
8492.797 Hz
8548.324 Hz
8554.361 Hz
8562.965 Hz
8578.193 Hz
8579.323 Hz
8579.333 Hz
8597.409 Hz
8642.181 Hz
8655.818 Hz
8758.341 Hz
8779.323 Hz
8792.231 Hz
8819.127 Hz
8831.132 Hz
8863.232 Hz
9028.031 Hz
9049.205 Hz
9173.264 Hz
9175.311 Hz
9184.338 Hz
9186.919 Hz
9393.946 Hz
9482.409 Hz
9658.296 Hz
9737.211 Hz
9746.232 Hz
9859.322 Hz
9922.231 Hz
10020.213 Hz
10032.684 Hz
10435.191 Hz
10446.028 Hz
10449.221 Hz
10457.329 Hz
10478.221 Hz
10498.339 Hz
10545.313 Hz
10639.345 Hz
10720.221 Hz
10743.118 Hz
10813.981 Hz
10832.421 Hz
10838.243 Hz
10862.429 Hz
10865.127 Hz
10917.229 Hz
10977.188 Hz
11120.209 Hz
11143.409 Hz
11177.289 Hz
11177.409 Hz
11321.491 Hz
11359.093 Hz
11540.212 Hz
11673.031 Hz
11731.295 Hz
11793.886 Hz
11895.229 Hz
12074.531 Hz
12216.212 Hz
12223.329 Hz
12243.132 Hz
12253.329 Hz
12260.933 Hz
12262.853 Hz
12292.222 Hz
12357.353 Hz
12527.032 Hz
12668.194 Hz
12743.197 Hz
12755.333 Hz
12947.311 Hz
13477.293 Hz
13582.122 Hz
13636.082 Hz
13717.221 Hz
13756.503 Hz
13825.295 Hz
13829.195 Hz
14188.611 Hz
14410.949 Hz
14436.201 Hz
14528.429 Hz
14537.218 Hz
14563.821 Hz
14835.809 Hz
14947.184 Hz
14948.323 Hz
15429.139 Hz
15443.309 Hz
15450.183 Hz
16026.221 Hz
16062.401 Hz
16081.291 Hz
16144.343 Hz
16331.323 Hz
17316.328 Hz
17930.967 Hz
17932.432 Hz
17951.395 Hz
17970.122 Hz
18242.181 Hz
18254.323 Hz
18265.238 Hz
18337.222 Hz
18344.212 Hz
18378.321 Hz
18921.415 Hz
18926.951 Hz
18931.327 Hz
19124.197 Hz
19133.123 Hz
19321.231 Hz
19686.593 Hz
114508.332 Hz

Example 4

AM Frequencies Employed for Treatment of Prostate Cancer (228 Frequencies so Far Included)

331.3 Hz
331.358 Hz
403.218 Hz
430.439 Hz
436.231 Hz
461.233 Hz
522.2 Hz
522.213 Hz
618.4 Hz
618.407 Hz
618.8 Hz
656.295 Hz
657.394 Hz
657.397 Hz
657.4 Hz
657.483 Hz
659.033 Hz
694.4 Hz
694.689 Hz
694.7 Hz
741.4 Hz
741.421 Hz
749.221 Hz
752.9 Hz
752.933 Hz
776.194 Hz
785.219 Hz
786.332 Hz
793.331 Hz
809.205 Hz
819.322 Hz
840.133 Hz
844.8 Hz
844.822 Hz
847.332 Hz
929.1 Hz
1083.309 Hz
1102.635 Hz
1102.71 Hz
1240.336 Hz
1372.934 Hz
1444.288 Hz
1486.322 Hz
1563.332 Hz
1591.322 Hz
1670.699 Hz
1697.321 Hz
1708.195 Hz
1741.939 Hz
1743.521 Hz
2031.448 Hz
2050.282 Hz
2076.519 Hz
2156.332 Hz
2229.515 Hz
2243.121 Hz
2381.443 Hz
2440.489 Hz
2475.912 Hz
2477.919 Hz
2551.332 Hz
2579.435 Hz
2628.324 Hz
2669.328 Hz
2824.832 Hz
2887.829 Hz
2891.331 Hz
3081.523 Hz
3133.309 Hz
3249.529 Hz
3250.125 Hz

-continued 3251.815 Hz
3264.827 Hz
3278.329 Hz
3281.432 Hz
3348.783 Hz
3519.118 Hz
3539.962 Hz
3551.318 Hz
3556.439 Hz
3572.321 Hz
3615.223 Hz
3670.129 Hz
3681.341 Hz
3686.021 Hz
3753.382 Hz
3774.923 Hz
3867.692 Hz
3909.333 Hz
3916.321 Hz
4031.233 Hz
4031.933 Hz
4038.203 Hz
4047.233 Hz
4066.222 Hz
4081.743 Hz
4084.319 Hz
4139.322 Hz
4153.192 Hz
4223.795 Hz
4231.221 Hz
4241.321 Hz
4320.513 Hz
4329.152 Hz
4380.321 Hz
4417.312 Hz
4489.452 Hz
4549.808 Hz
4558.306 Hz
4579.324 Hz
4638.293 Hz
4740.322 Hz
4854.318 Hz
4882.322 Hz
4978.822 Hz
5237.152 Hz
5264.222 Hz
5289.195 Hz
5426.323 Hz
5431.542 Hz
5455.593 Hz
6168.131 Hz
6345.332 Hz
6347.433 Hz
6363.284 Hz
6418.331 Hz
6496.231 Hz
6538.295 Hz
6577.421 Hz
6590.328 Hz
6651.276 Hz
6706.431 Hz
6743.322 Hz
6783.282 Hz
6850.197 Hz
6855.286 Hz
6864.896 Hz
6871.943 Hz
6878.356 Hz
6898.489 Hz
6973.393 Hz
7118.332 Hz
7120.932 Hz
7143.231 Hz
7146.509 Hz
7192.505 Hz
7251.309 Hz
7251.322 Hz
7278.124 Hz
7278.933 Hz 7279.335 Hz
7299.119 Hz
7527.229 Hz
7589.925 Hz
7699.193 Hz
7832.331 Hz
7842.184 Hz
7852.393 Hz
7872.333 Hz
8023.32 Hz
8096.939 Hz
8245.801 Hz
8315.291 Hz
8357.305 Hz
8408.121 Hz
8432.209 Hz
8535.238 Hz
8552.431 Hz
8585.224 Hz
8923.361 Hz
8935.752 Hz
9015.253 Hz
9018.233 Hz
9068.231 Hz
9137.232 Hz
9156.321 Hz
9351.931 Hz
9393.946 Hz
9694.179 Hz
9984.405 Hz
10226.223 Hz
10390.232 Hz
10442.221 Hz
10449.343 Hz
10459.084 Hz
10514.768 Hz
10651.311 Hz
10689.339 Hz
10772.419 Hz
10818.452 Hz
10843.543 Hz
11118.322 Hz
11165.239 Hz
11985.353 Hz
12209.329 Hz
12308.321 Hz
12489.233 Hz
12583.339 Hz
13820.329 Hz
14013.123 Hz
14129.213 Hz
14171.434 Hz
14681.329 Hz
14759.131 Hz
14986.794 Hz
15930.249 Hz
16026.623 Hz
16888.912 Hz
17091.189 Hz
17880.954 Hz
18021.222 Hz
18053.233 Hz
18247.532 Hz
18282.211 Hz
18610.232 Hz
18629.328 Hz
19469.318 Hz
19766.218 Hz
20159.434 Hz
21643.232 Hz
23022.481 Hz
23035.132 Hz
26718.23 Hz
30583.383 Hz
30653.323 Hz
30843.222 Hz
36065.221 Hz
60317.352 Hz

Example 5

AM Frequencies Employed for Treatment of Kidney Cancer (40 Frequencies so Far Included)

628.321 Hz
631.141 Hz
643.312 Hz
812.512 Hz
826.321 Hz
1240.336 Hz
1372.934 Hz
2082.241 Hz
2156.931 Hz
2254.329 Hz
2286.5 Hz
3555.209 Hz
3928.343 Hz
4329.152 Hz
4420.932 Hz
4819.228 Hz
4828.321 Hz
5314.322 Hz
6007.332 Hz
7054.279 Hz
7074.429 Hz
7254.343 Hz
8041.289 Hz
8727.224 Hz
8760.983 Hz
8831.132 Hz
8870.228 Hz
8923.1 Hz
10565.321 Hz
10586.229 Hz
10634.293 Hz
10687.949 Hz
11421.933 Hz
11523.212 Hz
11561.221 Hz
11846.212 Hz
12631.331 Hz
12693.272 Hz
14411.321 Hz
20178.941 Hz

Example 6

AM Frequencies Employed for Treatment of Thyroid Cancer (224 Frequencies so Far Included)

410.231 Hz
412.209 Hz
479.222 Hz
493.442 Hz
517.202 Hz
556.233 Hz
617.313 Hz
618.407 Hz
618.813 Hz
618.927 Hz
621.321 Hz
628.321 Hz
648.252 Hz
658.191 Hz
663.407 Hz
694.689 Hz
777.432 Hz
812.512 Hz
814.251 Hz
820.907 Hz
821.202 Hz
831.223 Hz

| | |
|---|---|
| 874.341 Hz | 4897.212 Hz |
| 914.429 Hz | 5323.192 Hz |
| 941.311 Hz | 5324.123 Hz |
| 942.331 Hz | 5548.879 Hz |
| 983.429 Hz | 5711.283 Hz |
| 1127.239 Hz | 5730.432 Hz |
| 1191.341 Hz | 5754.332 Hz |
| 1380.828 Hz | 5881.295 Hz |
| 1552.123 Hz | 5924.221 Hz |
| 1587.811 Hz | 6455.131 Hz |
| 1614.409 Hz | 6558.342 Hz |
| 1723.389 Hz | 6620.132 Hz |
| 1771.402 Hz | 6666.839 Hz |
| 2155.311 Hz | 6675.951 Hz |
| 2179.231 Hz | 6714.189 Hz |
| 2185.282 Hz | 6745.333 Hz |
| 2221.323 Hz | 6766.281 Hz |
| 2228.832 Hz | 6779.088 Hz |
| 2315.888 Hz | 6780.679 Hz |
| 2341.312 Hz | 6884.432 Hz |
| 2445.123 Hz | 6917.194 Hz |
| 2454.232 Hz | 6946.928 Hz |
| 2723.302 Hz | 7036.122 Hz |
| 2740.384 Hz | 7083.191 Hz |
| 2749.323 Hz | 7230.838 Hz |
| 2856.253 Hz | 7323.209 Hz |
| 2856.921 Hz | 7355.378 Hz |
| 2859.495 Hz | 7432.143 Hz |
| 2871.795 Hz | 7495.763 Hz |
| 2886.232 Hz | 7505.282 Hz |
| 2928.911 Hz | 7534.221 Hz |
| 2988.212 Hz | 7577.421 Hz |
| 3021.122 Hz | 7623.184 Hz |
| 3078.275 Hz | 7626.332 Hz |
| 3080.592 Hz | 7725.339 Hz |
| 3186.331 Hz | 7726.085 Hz |
| 3198.323 Hz | 7920.879 Hz |
| 3248.321 Hz | 8013.953 Hz |
| 3271.329 Hz | 8019.912 Hz |
| 3284.192 Hz | 8021.331 Hz |
| 3335.332 Hz | 8040.231 Hz |
| 3432.343 Hz | 8078.955 Hz |
| 3434.911 Hz | 8082.173 Hz |
| 3440.212 Hz | 8147.1 Hz |
| 3475.216 Hz | 8281.259 Hz |
| 3509.522 Hz | 8309.752 Hz |
| 3533.328 Hz | 8311.371 Hz |
| 3610.203 Hz | 8435.094 Hz |
| 3637.085 Hz | 8442.293 Hz |
| 3682.489 Hz | 8505.312 Hz |
| 3789.288 Hz | 8521.311 Hz |
| 3822.392 Hz | 8525.789 Hz |
| 3909.333 Hz | 8537.321 Hz |
| 3917.211 Hz | 8540.329 Hz |
| 4023.33 Hz | 8543.211 Hz |
| 4028.204 Hz | 8553.329 Hz |
| 4043.332 Hz | 8744.527 Hz |
| 4046.321 Hz | 8881.819 Hz |
| 4154.301 Hz | 9009.329 Hz |
| 4207.322 Hz | 9068.311 Hz |
| 4226.263 Hz | 9070.809 Hz |
| 4236.945 Hz | 9085.911 Hz |
| 4243.393 Hz | 9535.393 Hz |
| 4261.228 Hz | 9720.412 Hz |
| 4330.289 Hz | 10020.521 Hz |
| 4340.833 Hz | 10039.109 Hz |
| 4347.125 Hz | 10127.279 Hz |
| 4358.333 Hz | 10134.161 Hz |
| 4366.294 Hz | 10257.324 Hz |
| 4426.387 Hz | 10498.339 Hz |
| 4440.962 Hz | 10765.224 Hz |
| 4458.339 Hz | 10849.412 Hz |
| 4478.443 Hz | 10924.342 Hz |
| 4479.113 Hz | 10976.321 Hz |
| 4486.193 Hz | 11030.418 Hz |
| 4744.424 Hz | 11360.332 Hz |
| 4827.642 Hz | 11537.292 Hz |
| 4854.318 Hz | 11559.292 Hz |
| 4865.421 Hz | 11812.119 Hz |

-continued 11913.222 Hz
11927.934 Hz
11955.949 Hz
11960.179 Hz
12120.049 Hz
12139.222 Hz
12146.335 Hz
12489.233 Hz
12984.462 Hz
13425.229 Hz
13636.082 Hz
13654.272 Hz
13677.211 Hz
14014.941 Hz
14228.295 Hz
14445.214 Hz
14540.932 Hz
14823.325 Hz
14826.334 Hz
14910.894 Hz
15180.492 Hz
15561.322 Hz
15597.284 Hz
16023.119 Hz
16048.391 Hz
16080.831 Hz
16129.321 Hz
16539.532 Hz
17222.225 Hz
17253.222 Hz
17323.196 Hz
17461.504 Hz
17577.221 Hz
17671.321 Hz
17881.709 Hz
17911.323 Hz
17913.286 Hz
17937.203 Hz
17948.264 Hz
18036.921 Hz
18715.412 Hz
19859.429 Hz
21425.321 Hz
21452.445 Hz

Example 7

AM Frequencies Employed for Treatment of Bladder Cancer (31 Frequencies so Far Included)

623.243 Hz
757.084 Hz
870.4 Hz
2454.423 Hz
2480.191 Hz
2581.101 Hz
2715.232 Hz
3042.012 Hz
3196.194 Hz
3265.323 Hz
3438.109 Hz
3692.319 Hz
3952.308 Hz
5230.227 Hz
6022.942 Hz
6061.711 Hz
6710.899 Hz
6721.912 Hz
7181.784 Hz
7212.826 Hz
7458.209 Hz
8235.21 Hz
8749.232 Hz
8767.189 Hz

-continued 9354.812 Hz
9611.339 Hz
12532.729 Hz
13467.209 Hz
13777.9 Hz
14015.241 Hz
18524.419 Hz

Example 8

AM Frequencies Employed for Treatment of Colon Cancer (100 Frequencies so Far Included)

78.76 Hz
796.562 Hz
841.541 Hz
842.783 Hz
914.429 Hz
1162.117 Hz
1372.207 Hz
1372.934 Hz
1718.532 Hz
2243.169 Hz
2278.312 Hz
2286.5 Hz
2286.519 Hz
2334.178 Hz
2423.292 Hz
2454.423 Hz
2464.229 Hz
2598.853 Hz
2623.048 Hz
3131.123 Hz
3161.465 Hz
3175.313 Hz
3249.529 Hz
3363.229 Hz
3373.892 Hz
3390.925 Hz
3409.179 Hz
3432.274 Hz
3509.522 Hz
3531.422 Hz
3533.328 Hz
3766.296 Hz
4040.839 Hz
4081.022 Hz
4123.953 Hz
4146.274 Hz
4233.822 Hz
4282.332 Hz
4318.222 Hz
4344.082 Hz
4416.221 Hz
4481.242 Hz
4724.263 Hz
4751.319 Hz
4755.323 Hz
4788.485 Hz
5149.331 Hz
5217.402 Hz
5386.212 Hz
5407.192 Hz
5426.323 Hz
5496.434 Hz
5555.212 Hz
5572.032 Hz
5634.933 Hz
5724.231 Hz
5758.378 Hz
5787.342 Hz
5948.897 Hz
5967.448 Hz
5976.825 Hz

-continued 6182.322 Hz
6292.379 Hz
6324.493 Hz
6341.248 Hz
6471.322 Hz
6477.218 Hz
6558.342 Hz
6855.286 Hz
7129.843 Hz
7140.187 Hz
7162.422 Hz
7368.222 Hz
7645.859 Hz
7829.234 Hz
7866.229 Hz
7877.334 Hz
8013.314 Hz
8374.942 Hz
8384.228 Hz
8408.121 Hz
8534.111 Hz
8568.033 Hz
8573.122 Hz
9226.222 Hz
9351.9 Hz
9737.211 Hz
9744.193 Hz
9942.321 Hz
10301.371 Hz
10401.515 Hz
10872.693 Hz
11220.222 Hz
11283.378 Hz
12256.432 Hz
13749.858 Hz
15231.548 Hz
15248.324 Hz
58191.928 Hz
60317.352 Hz Example 9

AM Frequencies Employed for Treatment of Pancreas Cancer (166 Frequencies so Far Included)

331.3 Hz
331.365 Hz
436.3 Hz
436.332 Hz
447.942 Hz
476.127 Hz
559.292 Hz
589.187 Hz
624.218 Hz
727 Hz
734.921 Hz
809.313 Hz
845.309 Hz
870.4 Hz
963.221 Hz
1156.79 Hz
1157 Hz
1179 Hz
1360.133 Hz
1372.207 Hz
1372.934 Hz
1804.126 Hz
1816.221 Hz
1873.477 Hz
1967.211 Hz
1990.482 Hz
2278.312 Hz
2315.921 Hz
2320.315 Hz

-continued 2334.178 Hz
2381.443 Hz
2469 Hz
2477.919 Hz
2542.221 Hz
2598.853 Hz
2647.938 Hz
2685.081 Hz
2716.095 Hz
2721.331 Hz
2732.231 Hz
2809.849 Hz
2823.428 Hz
2835.332 Hz
3134.313 Hz
3241.461 Hz
3255.219 Hz
3263.432 Hz
3286.255 Hz
3330.935 Hz
3373.892 Hz
3438.109 Hz
3449.219 Hz
3535.219 Hz
3549.215 Hz
3564.419 Hz
3619.412 Hz
3622.312 Hz
3638.432 Hz
3696.424 Hz
3943.214 Hz
3976.929 Hz
4014.889 Hz
4041.219 Hz
4044.195 Hz
4056.384 Hz
4085.971 Hz
4144.592 Hz
4153.192 Hz
4161.889 Hz
4243.393 Hz
4332.498 Hz
4341.423 Hz
4355.327 Hz
4417.885 Hz
4422.322 Hz
4451.297 Hz
4486.384 Hz
4558.306 Hz
4580 Hz
4685.082 Hz
4839.589 Hz
5151.402 Hz
5209.911 Hz
5262.282 Hz
5271.312 Hz
5387.73 Hz
5494.928 Hz
5521.221 Hz
5573.209 Hz
5609.382 Hz
5929.616 Hz
5948.897 Hz
5966.112 Hz
5976.825 Hz
6064.197 Hz
6086.256 Hz
6157.253 Hz
6215.298 Hz
6333.917 Hz
6365.242 Hz
6558.342 Hz
6568.278 Hz
6823.194 Hz
6853.391 Hz
6855.286 Hz
7213.204 Hz
7228.528 Hz
7238.232 Hz 7277.921 Hz
7280.422 Hz
7320.494 Hz
7366.412 Hz
7534.221 Hz
7548.713 Hz
7567.127 Hz
7620.851 Hz
7663.209 Hz
7725.203 Hz
7852.233 Hz
7920.879 Hz
7985.122 Hz
8008.323 Hz
8013.312 Hz
8045.484 Hz
8242.332 Hz
8351.622 Hz
8408.121 Hz
8455.894 Hz
8551.231 Hz
8743.321 Hz
8789.631 Hz
8868.809 Hz
9012.241 Hz
9028.994 Hz
9131.232 Hz
9658.296 Hz
9663.495 Hz
9680.737 Hz
9824.442 Hz
9942.321 Hz
10279.122 Hz
10388.49 Hz
10438.495 Hz
10518.311 Hz
10528.239 Hz
10582.095 Hz
10926.111 Hz
10948.411 Hz
10955.558 Hz
11538.193 Hz
11904.741 Hz
12255.229 Hz
12613.341 Hz
12819.942 Hz
13674.482 Hz
13731.322 Hz
14525.312 Hz
14537.218 Hz
14549.331 Hz
14845.453 Hz
14944.989 Hz
15246.315 Hz
18668.239 Hz
19321.231 Hz
19347.208 Hz
30182.932 Hz Example 10

AM Frequencies Employed for Treatment of Lung Cancer (80 Frequencies so Far Included)

304.148 Hz
694.7 Hz
694.727 Hz
708.8 Hz
708.841 Hz
1587.811 Hz
1759.318 Hz
1873.477 Hz
2253.704 Hz
2391.312 Hz
2454.232 Hz
2729.929 Hz
2741.261 Hz
2761.312 Hz
2784.491 Hz
2812.443 Hz
2855.218 Hz
2859.495 Hz
3128.822 Hz
3139.297 Hz
3193.212 Hz
3348.783 Hz
3360.971 Hz
3366.311 Hz
3373.892 Hz
3440.212 Hz
3461.322 Hz
3682.489 Hz
3727.231 Hz
3749.882 Hz
3769.942 Hz
4131.235 Hz
4158.393 Hz
4243.393 Hz
4347.733 Hz
4373.411 Hz
4378.321 Hz
4416.221 Hz
4481.242 Hz
4777.521 Hz
4798.422 Hz
4837.241 Hz
4959.842 Hz
5013.321 Hz
5047.523 Hz
5068.322 Hz
5371.922 Hz
5538.432 Hz
5548.879 Hz
5679.309 Hz
5734.143 Hz
5787.342 Hz
6445.309 Hz
6838.434 Hz
6870.955 Hz
6879.216 Hz
7079.411 Hz
7216.288 Hz
7376.089 Hz
7761.289 Hz
8082.173 Hz
8281.259 Hz
8352.189 Hz
8442.473 Hz
8773.916 Hz
8935.752 Hz
9121.223 Hz
9181.434 Hz
9317.913 Hz
9363.896 Hz
9736.919 Hz
9753.321 Hz
10424.908 Hz
10452.913 Hz
10824.609 Hz
11656.329 Hz
12748.919 Hz
15774.291 Hz
15798.333 Hz
16510.333 Hz

Example 11

AM Frequencies Employed for Treatment of Leiomyosarcoma (36 Frequencies so Far Included)

836.923 Hz
843.181 Hz
1411.241 Hz
2073.721 Hz
2381.443 Hz
2711.019 Hz
2911.329 Hz
3232.185 Hz
3518.321 Hz
3544.209 Hz
3569.219 Hz
4233.822 Hz
4241.321 Hz
4266.591 Hz
4337.322 Hz
4424.112 Hz
4436.111 Hz
4485.22 Hz
5545.521 Hz
5577.841 Hz
5631.422 Hz
5696.184 Hz
6472.098 Hz
6558.342 Hz
6651.276 Hz
7168.892 Hz
7406.309 Hz
7452.528 Hz
7649.209 Hz
7808.352 Hz
9040.313 Hz
9074.294 Hz
9189.092 Hz
9484.512 Hz
9943.972 Hz
12086.394 Hz

Example 12

AM Frequencies Employed for Treatment of Mesothelioma (16 Frequencies so Far Included)

958.929 Hz
1713.913 Hz
1736.782 Hz
2334.178 Hz
2607.193 Hz
3112.974 Hz
3319.945 Hz
3449.219 Hz
3622.312 Hz
5151.402 Hz
5887.022 Hz
5965.922 Hz
6516.793 Hz
7224.197 Hz
9471.152 Hz
14617.393 Hz

Example 13

AM Frequencies Employed for Treatment of Neuro-Endocrine (30 Frequencies so Far Included)

1766.335 Hz
2408.225 Hz
2441.502 Hz
2647.938 Hz
2741.261 Hz
3020.212 Hz
3128.822 Hz
3238.742 Hz
3296.431 Hz
3348.783 Hz
3360.971 Hz
3440.212 Hz
3533.328 Hz
3666.283 Hz
4079.282 Hz
4243.393 Hz
4426.387 Hz
5245.818 Hz
5536.242 Hz
5548.879 Hz
5739.422 Hz
5849.241 Hz
6291.631 Hz
6406.891 Hz
6780.679 Hz
7151.264 Hz
7482.245 Hz
7575.393 Hz
8359.932 Hz
9073.418 Hz

Example 14

AM Frequencies Employed for Treatment of Leukemia and Chronic Lymphoid Cancer (17 Frequencies so Far Included)

814.413 Hz
825.145 Hz
2415.243 Hz
2436.316 Hz
2874.432 Hz
2891.029 Hz
3361.671 Hz
5245.452 Hz
5557.333 Hz
6850.197 Hz
6919.322 Hz
7587.224 Hz
7629.318 Hz
8172.405 Hz
8272.338 Hz
8438.453 Hz
12950.331 Hz

Example 15

AM Frequencies Employed for Treatment of Myeloma, Multiple Cancer (20 Frequencies so Far Included)

765.196 Hz
2336.238 Hz
2372.122 Hz
2381.443 Hz
2425.394 Hz
2656.339 Hz
2741.261 Hz
2883.618 Hz
2919.273 Hz
3265.323 Hz
3564.455 Hz
3580.25 Hz
3584.291 Hz
3674.292 Hz

-continued

| |
|---|
| 5249.331 Hz |
| 7967.311 Hz |
| 7973.125 Hz |
| 8049.952 Hz |
| 8283.329 Hz |
| 10351.323 Hz |

Example 16

AM Frequencies Employed for Treatment of Hodgkin Disease (Lymphoma) (19 Frequencies so Far Included)

| |
|---|
| 752.5 Hz |
| 976.3 Hz |
| 1558.223 Hz |
| 2310.912 Hz |
| 2477.919 Hz |
| 2560.843 Hz |
| 3348.783 Hz |
| 3371.216 Hz |
| 3605.432 Hz |
| 3623.198 Hz |
| 3838.281 Hz |
| 3838.48 Hz |
| 5102 Hz |
| 5696.932 Hz |
| 5724.231 Hz |
| 6358.194 Hz |
| 7472.211 Hz |
| 8062.121 Hz |
| 8222.222 Hz |

Example 17

AM Frequencies Employed for Treatment of Brain Cancer (57 Frequencies so Far Included)

| |
|---|
| 1372.934 Hz |
| 2318.182 Hz |
| 2381.443 Hz |
| 2425.394 Hz |
| 2442.423 Hz |
| 2478.973 Hz |
| 2654.513 Hz |
| 2661.324 Hz |
| 2686.105 Hz |
| 2690.179 Hz |
| 3249.332 Hz |
| 3277.509 Hz |
| 3335.279 Hz |
| 3348.783 Hz |
| 3436.211 Hz |
| 3916.321 Hz |
| 4031.933 Hz |
| 4086.091 Hz |
| 4241.321 Hz |
| 4318.222 Hz |
| 4334.33 Hz |
| 4358.333 Hz |
| 4393.419 Hz |
| 4454.194 Hz |
| 4515.789 Hz |
| 4619.324 Hz |
| 4723.937 Hz |
| 4853.286 Hz |
| 5289.231 Hz |

-continued

| |
|---|
| 5378.099 Hz |
| 5426.323 Hz |
| 5640.981 Hz |
| 6316.211 Hz |
| 6459.203 Hz |
| 6474.332 Hz |
| 6626.572 Hz |
| 6855.286 Hz |
| 6915.886 Hz |
| 6943.386 Hz |
| 7151.264 Hz |
| 7182.922 Hz |
| 7194.897 Hz |
| 7323.209 Hz |
| 7390.343 Hz |
| 7796.221 Hz |
| 7961.122 Hz |
| 8128.942 Hz |
| 8245.109 Hz |
| 8272.281 Hz |
| 8358.154 Hz |
| 8408.121 Hz |
| 9138.82 Hz |
| 10719.318 Hz |
| 11556.241 Hz |
| 12828.633 Hz |
| 14515.962 Hz |
| 14586.765 Hz |

The above Examples reflect AM frequencies determined by a bio-feedback procedure involving very substantial observations and measurements of physiological responses (at certain well defined AM frequencies) by subjects exposed to low energy electromagnetic emission excitation. In general, it is recommended that all of the listed frequencies be applied in the treatment of subjects suffering from the indicated form of cancer. However, a limited number of the listed frequencies also lead to beneficial effects.

Of note in respect of the above listed frequencies, in particular those Examples including a large number of frequencies, it has earlier on been determined that beneficial therapeutic effects are achieved by application of some but not all of the frequencies listed. However, following on more extended trials, it has been determined that application to subjects of further frequencies enhance the efficacy of treatment and yields therapeutic effects in patients whose tumors have become resistant to therapy. It is accordingly preferred that all of the determined listed frequencies be applied to the subject. The mechanism of including additional frequencies is attributed to either or both of inter-active synergism between applied frequencies or between cells which have been influenced by the treatment and additive effects of the additional frequencies.

Of further note is the fact that different patients suffering from the same type of tumor cell growth practically invariably exhibit the above-mentioned physiological responses at the same well defined AM frequencies. Furthermore, AM frequencies which differ only very slightly (less than 0.0001% at higher frequencies) from the frequencies listed, in general elicit no physiological response by subjects exposed to excitation at such very slightly different frequency. In view of these determinations, the electronic system of the present invention may be adapted to screen a subject for physiological responses over a broad range of frequencies to determine the presence or absence tumor cells and, if positive, then to note at which defined frequencies physiological responses are elicited. These frequencies will in general match with the defined frequencies listed in one or other of the Examples above or such further examples as may be developed and hence the nature of the tumor will be known. The electronic system of the invention is therefore a valuable diagnostic tool for diagnosing the presence or absence and identities of types of tumor cell growths or cancers. Furthermore, the electronic system of the invention is of value for predicting whether a patient will benefit from the application of a given series of modulation frequencies. The system therefore possesses a capability of predicting responses to treatment, thereby enhancing the possibility to select optimal modes. of treatment.

The sequence of well defined frequencies are preferably applied sequentially for determined periods of time, e.g., 3 seconds for each frequency, but several frequencies may also be applied simultaneously. This means that a cycle of application involving 180 frequencies would take nearly 10 minutes time. Advantageous effects may however also arise from applying individual well defined frequencies for differing time periods, e.g., some for 3 seconds, some for 6 seconds, etc.

Therapeutic dosages to be applied to a subject suffering from the presence of tumor cell growth or cancer are determined by the time of application of the low energy electromagnetic emissions to the subject and will depend on the nature of the cancer and the overall condition of the subject. In general, however, greatest experience has been gained in treating terminally ill subjects expected to survive no longer than about three months and who have agreed to discontinue alternative forms of cancer treatments such as chemo-therapy or radioactive treatment. In these severe cases, lengthy times of treatment are recommended, e.g., 3 times 1 hour daily treatment. However, with the development of alternative forms of application, i.e., other than by means of a mouth probe, continuous application is possible and is likely to enhance compliance and the efficacy of the treatment.

While the invention has been described with specific embodiments, other alternatives, modifications and variations will be apparent to those skilled in the art. Accordingly, it will be intended to include all such alternatives, modifications, and variations within the spirit and scope of the appended claims.

It is claimed:

1. An electronic system activatable by electrical power and structured to inhibit proliferation of cancerous cells or to kill cancerous cells harboured by a warm-blooded mammalian subject, said electronic system comprising at least one controllable low energy electromagnetic energy generator circuit for generating one or more high frequency carrier signals, at least one data processor constructed and arranged for communication with the at least one generator circuit and for receiving control information from a source of control information, said at least one generator circuit including at least one amplitude modulation control signal generator for controlling amplitude modulated variations of the one or more high frequency carrier signals, said at least one generator circuit furthermore including at least one programmable amplitude modulation frequency control signal generator for controlling frequencies at which amplitude modulations are generated, the system furthermore comprising a connection position for connection to an electrically conductive applicator for applying to the warm-blooded mammalian subject one or more amplitude-modulated low energy emissions at a program-controlled frequency, wherein said at least one programmable amplitude frequency control generator is adapted to accurately control the frequencies at which said amplitude modulations are generated to within an accuracy of at least 1000 parts per million relative to determined or predetermined reference amplitude modulation frequencies selected from within a range of 0.01 Hz to 150 kHz and wherein said source of control information includes reference amplitude modulation frequency control information which comprises a selection of from at least a proportion in excess of 50% to all of reference amplitude modulation frequencies accurately defined for a type of the cancerous cells to be inhibited in proliferation or killed, wherein said selection of the reference amplitude modulation frequencies accurately defined comprised in said source control information is made dependent on the type of cancerous cells to be inhibited in proliferation or killed identified as set forth in combination with listings of the reference amplitude modulation frequencies accurately defined as follows:

(1) frequencies for treatment of breast cancer as follows 78.76 Hz
181.821 Hz
331.3 Hz
414.817 Hz
430.439 Hz
440.933 Hz
618.8 Hz
628.431 Hz
655.435 Hz
677.972 Hz
721.313 Hz
752.933 Hz
813.205 Hz
818.342 Hz
825.145 Hz
839.521 Hz
841.211 Hz
843.312 Hz
891.901 Hz
929.095 Hz
929.1 Hz
929.131 Hz
958.929 Hz
1021 Hz
1021.311 Hz
1156.79 Hz
1372.207 Hz
1372.934 Hz
1555.282 Hz
1588.721 Hz
1624.802 Hz
1670.699 Hz
1821.729 Hz
1836.219 Hz
2193.937 Hz
2221.323 Hz
2278.312 Hz
2332.949 Hz
2357.832 Hz
2381.443 Hz
2417.323 Hz
2423.292 Hz
2431.334 Hz
2450.332 Hz
2551.313 Hz
2556.221 Hz
2598.853 Hz
2621.322 Hz
2740.191 Hz
2823.428 Hz
2831.386 Hz
2851.347 Hz
2885.322 Hz
2919.273 Hz
3074.333 Hz
3115.188 Hz
3239.212 Hz
3249.529 Hz
3405.182 Hz
3432.274 Hz
3434.693 Hz
3594.231 Hz
3647.619 Hz -continued

| | |
|---|---|
| 3657.931 Hz | 7621.085 Hz |
| 3742.957 Hz | 7627.207 Hz |
| 3753.382 Hz | 7650.939 Hz |
| 3830.732 Hz | 7668.231 Hz |
| 3855.823 Hz | 7691.212 Hz |
| 3916.321 Hz | 7842.184 Hz |
| 3935.218 Hz | 7849.231 Hz |
| 3975.383 Hz | 7915.423 Hz |
| 3993.437 Hz | 7932.482 Hz |
| 4153.192 Hz | 7949.196 Hz |
| 4194.968 Hz | 7967.311 Hz |
| 4241.321 Hz | 8021.229 Hz |
| 4243.393 Hz | 8070.181 Hz |
| 4253.432 Hz | 8114.032 Hz |
| 4314.444 Hz | 8149.922 Hz |
| 4318.222 Hz | 8194.19 Hz |
| 4375.962 Hz | 8245.801 Hz |
| 4393.419 Hz | 8328.322 Hz |
| 4394.134 Hz | 8330.534 Hz |
| 4417.243 Hz | 8355.987 Hz |
| 4481.463 Hz | 8408.121 Hz |
| 4482.223 Hz | 8431.184 Hz |
| 4495.138 Hz | 8452.119 Hz |
| 4549.808 Hz | 8548.324 Hz |
| 4558.306 Hz | 8749.383 Hz |
| 4751.908 Hz | 8782.421 Hz |
| 4779.451 Hz | 8784.424 Hz |
| 4838.674 Hz | 8887.182 Hz |
| 4871.513 Hz | 8894.222 Hz |
| 4878.687 Hz | 8923.1 Hz |
| 4895.296 Hz | 8923.361 Hz |
| 4962.213 Hz | 8935.752 Hz |
| 4969.224 Hz | 8936.1 Hz |
| 4979.321 Hz | 9012.282 Hz |
| 5027.231 Hz | 9012.896 Hz |
| 5059.792 Hz | 9060.323 Hz |
| 5118.094 Hz | 9072.409 Hz |
| 5176.287 Hz | 9131.419 Hz |
| 5365.222 Hz | 9199.232 Hz |
| 5376.392 Hz | 9245.927 Hz |
| 5426.323 Hz | 9270.322 Hz |
| 5431.542 Hz | 9279.193 Hz |
| 5521.621 Hz | 9393.946 Hz |
| 5536.242 Hz | 10227.242 Hz |
| 5739.422 Hz | 10340.509 Hz |
| 5745.218 Hz | 10363.313 Hz |
| 5821.975 Hz | 10449.323 Hz |
| 6037.432 Hz | 10456.383 Hz |
| 6044.333 Hz | 10468.231 Hz |
| 6086.256 Hz | 10470.456 Hz |
| 6208.932 Hz | 10472.291 Hz |
| 6212.808 Hz | 10689.339 Hz |
| 6231.031 Hz | 10832.222 Hz |
| 6280.321 Hz | 11525.121 Hz |
| 6329.391 Hz | 11541.915 Hz |
| 6476.896 Hz | 11812.328 Hz |
| 6477.098 Hz | 11812.419 Hz |
| 6497.319 Hz | 11840.323 Hz |
| 6504.983 Hz | 11925.089 Hz |
| 6651.276 Hz | 12123.281 Hz |
| 6657.913 Hz | 12267.281 Hz |
| 6757.901 Hz | 12294.283 Hz |
| 6758.321 Hz | 12334.419 Hz |
| 6855.286 Hz | 12611.288 Hz |
| 6858.121 Hz | 12629.222 Hz |
| 6898.489 Hz | 12633.372 Hz |
| 6915.886 Hz | 12648.221 Hz |
| 7092.219 Hz | 13315.335 Hz |
| 7120.218 Hz | 13331.358 Hz |
| 7127.311 Hz | 13735.241 Hz |
| 7156.489 Hz | 13826.325 Hz |
| 7208.821 Hz | 13853.232 Hz |
| 7224.197 Hz | 13915.231 Hz |
| 7282.169 Hz | 13990.123 Hz |
| 7285.693 Hz | 14122.942 Hz |
| 7376.329 Hz | 14162.332 Hz |
| 7488.742 Hz | 14519.232 Hz |
| 7541.319 Hz | 14543.128 Hz |
| 7577.421 Hz | 15651.323 Hz |

17352.085 Hz
17970.122 Hz
18524.419 Hz
18619.331 Hz
18662.112 Hz
18679.492 Hz
18785.463 Hz
19385.893 Hz
19406.211 Hz
22479.333 Hz
30182.932 Hz;

(2) frequencies for treatment of hepatocellular carcinoma (liver cancer) as follows 380.293 Hz
410.231 Hz
423.321 Hz
427.062 Hz
434.332 Hz
470.181 Hz
560.32 Hz
642.932 Hz
655.435 Hz
657.394 Hz
668.209 Hz
677.972 Hz
728.232 Hz
806.021 Hz
811.924 Hz
842.311 Hz
843.22 Hz
845.208 Hz
891.901 Hz
914.219 Hz
920.321 Hz
964.394 Hz
1250.504 Hz
1755.402 Hz
1814.223 Hz
1851.202 Hz
1873.477 Hz
1924.702 Hz
1975.196 Hz
2017.962 Hz
2053.396 Hz
2083.419 Hz
2190.731 Hz
2221.323 Hz
2308.294 Hz
2315.208 Hz
2324.393 Hz
2338.221 Hz
2353.478 Hz
2362.309 Hz
2379.571 Hz
2419.309 Hz
2425.222 Hz
2430.219 Hz
2431.094 Hz
2471.328 Hz
2478.331 Hz
2480.191 Hz
2522.328 Hz
2743.995 Hz
2744.211 Hz
2831.951 Hz
2843.283 Hz
2859.891 Hz
2873.542 Hz
2886.232 Hz
3009.332 Hz
3020.286 Hz
3042.012 Hz
3044.213 Hz
3051.218 Hz
3076.892 Hz
3078.983 Hz
3086.443 Hz
3104.854 Hz
3127.232 Hz
3160.942 Hz
3161.331 Hz
3167.22 Hz
3206.315 Hz
3255.219 Hz
3267.433 Hz
3269.321 Hz
3281.432 Hz
3457.291 Hz
3505.229 Hz
3516.296 Hz
3530.188 Hz
3531.296 Hz
3546.323 Hz
3572.106 Hz
3576.189 Hz
3669.513 Hz
3923.221 Hz
3927.331 Hz
4013.932 Hz
4071.121 Hz
4079.951 Hz
4123.953 Hz
4161.889 Hz
4222.821 Hz
4238.402 Hz
4256.321 Hz
4289.296 Hz
4312.947 Hz
4375.962 Hz
4426.387 Hz
4428.185 Hz
4435.219 Hz
4471.188 Hz
4483.889 Hz
4486.384 Hz
4556.322 Hz
4629.941 Hz
4715.222 Hz
4732.211 Hz
4767.185 Hz
4873.333 Hz
4876.218 Hz
5086.281 Hz
5124.084 Hz
5133.121 Hz
5247.142 Hz
5270.834 Hz
5340.497 Hz
5520.218 Hz
5570.234 Hz
5882.292 Hz
5926.512 Hz
6037.311 Hz
6180.334 Hz
6329.195 Hz
6350.333 Hz
6361.321 Hz
6364.928 Hz
6383.321 Hz
6461.175 Hz
6661.109 Hz
6711.392 Hz
6733.331 Hz
6758.232 Hz
6779.482 Hz
6856.222 Hz
6877.183 Hz
6915.886 Hz
6980.525 Hz
7019.235 Hz
7041.321 Hz
7043.209 Hz
7078.307 Hz
7130.323 Hz -continued 7144.142 Hz
7210.223 Hz
7232.343 Hz
7291.21 Hz
7482.245 Hz
7510.92 Hz
7529.233 Hz
7549.212 Hz
7650.028 Hz
7680.518 Hz
7692.522 Hz
7829.231 Hz
7862.209 Hz
7932.482 Hz
7935.423 Hz
7947.392 Hz
7979.308 Hz
8025.322 Hz
8028.339 Hz
8055.942 Hz
8072.134 Hz
8141.174 Hz
8208.285 Hz
8328.312 Hz
8336.383 Hz
8394.793 Hz
8432.181 Hz
8452.119 Hz
8460.944 Hz
8475.221 Hz
8492.193 Hz
8542.311 Hz
8779.229 Hz
8818.104 Hz
8852.329 Hz
8853.444 Hz
8858.179 Hz
8915.221 Hz
8939.212 Hz
8953.231 Hz
8993.239 Hz
9278.889 Hz
9332.397 Hz
9381.221 Hz
9520.333 Hz
9719.314 Hz
9740.219 Hz
9768.331 Hz
9773.111 Hz
9797.294 Hz
9819.511 Hz
9845.319 Hz
10015.419 Hz
10043.293 Hz
10317.499 Hz
10438.495 Hz
10443.311 Hz
10456.383 Hz
10579.425 Hz
10863.209 Hz
10866.382 Hz
11067.418 Hz
11149.935 Hz
11163.895 Hz
11195.509 Hz
11421.219 Hz
11802.821 Hz
11953.424 Hz
12024.502 Hz
12223.329 Hz
12228.369 Hz
12247.233 Hz
12260.933 Hz
12265.295 Hz
12267.233 Hz
12267.296 Hz
12274.219 Hz
12623.191 Hz
12633.372 Hz -continued 12685.231 Hz
12721.423 Hz
12785.342 Hz
13433.323 Hz
13457.388 Hz
14085.222 Hz
14212.122 Hz
14226.313 Hz
14333.209 Hz
14537.331 Hz
14542.432 Hz
14655.03 Hz
14736.223 Hz
14828.234 Hz
15149.213 Hz
15237.489 Hz
15560.908 Hz
15717.221 Hz
16110.932 Hz
16144.343 Hz
17153.322 Hz
17660.109 Hz
18121.184 Hz
18265.238 Hz
18283.323 Hz
18863.292 Hz
18930.995 Hz
19970.311 Hz
20330.294 Hz
20365.284 Hz
22321.331 Hz
24119.295 Hz
24181.221 Hz;

(3) frequencies for treatment of ovarian cancer as follows 78.76 Hz
181.821 Hz
367.211 Hz
403.218 Hz
410.245 Hz
414.817 Hz
436.332 Hz
447.942 Hz
481.191 Hz
489.292 Hz
537.914 Hz
559.292 Hz
608.321 Hz
618.407 Hz
621.321 Hz
655.435 Hz
657.394 Hz
657.397 Hz
657.483 Hz
664.211 Hz
694.689 Hz
708.787 Hz
708.8 Hz
708.821 Hz
708.822 Hz
734.921 Hz
749.221 Hz
764.232 Hz
778.295 Hz
779.403 Hz
806.021 Hz
806.389 Hz
809.313 Hz
824.327 Hz
825.145 Hz
835.129 Hz
839.521 Hz
841.208 Hz
843.312 Hz
925.309 Hz
956.984 Hz -continued 958.929 Hz
985.313 Hz
1024.208 Hz
1102.635 Hz
1121.329 Hz
1159.738 Hz
1221.321 Hz
1372.207 Hz
1396.498 Hz
1502.181 Hz
1518.208 Hz
1552.123 Hz
1579.212 Hz
1624.802 Hz
1656.431 Hz
1670.699 Hz
1679.432 Hz
1696.403 Hz
1759.318 Hz
1762.938 Hz
1771.402 Hz
1775.313 Hz
1821.729 Hz
1990.482 Hz
2016.323 Hz
2031.448 Hz
2034.231 Hz
2050.282 Hz
2053.396 Hz
2082.234 Hz
2089.092 Hz
2221.323 Hz
2228.832 Hz
2229.515 Hz
2253.704 Hz
2254.329 Hz
2278.312 Hz
2332.949 Hz
2348.233 Hz
2381.443 Hz
2413.193 Hz
2415.243 Hz
2425.222 Hz
2433.321 Hz
2439.253 Hz
2465.23 Hz
2477.919 Hz
2669.177 Hz
2715.232 Hz
2733.843 Hz
2771.211 Hz
2802.339 Hz
2812.321 Hz
2831.386 Hz
2835.332 Hz
2851.347 Hz
2856.253 Hz
2873.542 Hz
2877.192 Hz
2885.322 Hz
2887.385 Hz
2894.972 Hz
2973.771 Hz
3080.592 Hz
3157.483 Hz
3160.321 Hz
3161.465 Hz
3185.129 Hz
3223.232 Hz
3238.148 Hz
3240.111 Hz
3249.529 Hz
3254.122 Hz
3262.145 Hz
3264.241 Hz
3265.121 Hz
3282.235 Hz
3283.392 Hz
3296.431 Hz -continued 3314.321 Hz
3361.671 Hz
3366.311 Hz
3459.408 Hz
3461.322 Hz
3523.215 Hz
3527.233 Hz
3542.213 Hz
3590.376 Hz
3629.232 Hz
3632.793 Hz
3636.289 Hz
3637.085 Hz
3669.513 Hz
3770.189 Hz
3858.916 Hz
3872.321 Hz
3919.232 Hz
3941.739 Hz
3957.185 Hz
3975.228 Hz
3975.383 Hz
4061.131 Hz
4072.322 Hz
4139.322 Hz
4169.451 Hz
4174.259 Hz
4241.321 Hz
4243.393 Hz
4261.228 Hz
4279.113 Hz
4309.335 Hz
4314.188 Hz
4318.222 Hz
4328.928 Hz
4340.833 Hz
4380.321 Hz
4394.134 Hz
4412.252 Hz
4424.236 Hz
4439.341 Hz
4442.161 Hz
4447.221 Hz
4458.339 Hz
4556.322 Hz
4566.009 Hz
4579.981 Hz
4682.643 Hz
4718.331 Hz
4749.302 Hz
4765.331 Hz
4779.194 Hz
4912.923 Hz
4917.202 Hz
5011.325 Hz
5149.331 Hz
5228.172 Hz
5237.132 Hz
5313.353 Hz
5745.218 Hz
5757.897 Hz
5762.386 Hz
5812.322 Hz
5869.321 Hz
5882.292 Hz
5921.249 Hz
5991.932 Hz
6069.458 Hz
6071.319 Hz
6083.214 Hz
6111.819 Hz
6161.782 Hz
6169.341 Hz
6275.232 Hz
6294.929 Hz
6350.333 Hz
6356.321 Hz
6406.891 Hz
6407.207 Hz

| 49 | 50 |
|---|---|
| -continued | -continued |

| | |
|---|---|
| 6450.787 Hz | 9482.409 Hz |
| 6477.098 Hz | 9658.296 Hz |
| 6477.929 Hz | 9737.211 Hz |
| 6478.338 Hz | 9746.232 Hz |
| 6504.983 Hz | 9859.322 Hz |
| 6543.421 Hz | 9922.231 Hz |
| 6552.24 Hz | 10020.213 Hz |
| 6661.09 Hz | 10032.684 Hz |
| 6663.955 Hz | 10435.191 Hz |
| 6753.338 Hz | 10446.028 Hz |
| 6789.211 Hz | 10449.221 Hz |
| 6851.323 Hz | 10457.329 Hz |
| 6855.286 Hz | 10478.221 Hz |
| 6875.232 Hz | 10498.339 Hz |
| 6882.949 Hz | 10545.313 Hz |
| 7047.223 Hz | 10639.345 Hz |
| 7206.403 Hz | 10720.221 Hz |
| 7232.214 Hz | 10743.118 Hz |
| 7257.489 Hz | 10813.981 Hz |
| 7276.209 Hz | 10832.421 Hz |
| 7279.335 Hz | 10838.243 Hz |
| 7281.219 Hz | 10862.429 Hz |
| 7285.223 Hz | 10865.127 Hz |
| 7285.693 Hz | 10917.229 Hz |
| 7289.192 Hz | 10977.188 Hz |
| 7326.229 Hz | 11120.209 Hz |
| 7399.223 Hz | 11143.409 Hz |
| 7429.212 Hz | 11177.289 Hz |
| 7460.932 Hz | 11177.409 Hz |
| 7480.228 Hz | 11321.491 Hz |
| 7488.742 Hz | 11359.093 Hz |
| 7495.763 Hz | 11540.212 Hz |
| 7539.432 Hz | 11673.031 Hz |
| 7564.185 Hz | 11731.295 Hz |
| 7650.028 Hz | 11793.886 Hz |
| 7689.728 Hz | 11895.229 Hz |
| 7780.294 Hz | 12074.531 Hz |
| 8021.921 Hz | 12216.212 Hz |
| 8038.961 Hz | 12223.329 Hz |
| 8040.322 Hz | 12243.132 Hz |
| 8044.233 Hz | 12253.329 Hz |
| 8054.413 Hz | 12260.933 Hz |
| 8095.313 Hz | 12262.853 Hz |
| 8141.174 Hz | 12292.222 Hz |
| 8143.491 Hz | 12357.353 Hz |
| 8164.332 Hz | 12527.032 Hz |
| 8261.121 Hz | 12668.194 Hz |
| 8302.285 Hz | 12743.197 Hz |
| 8309.752 Hz | 12755.333 Hz |
| 8372.532 Hz | 12947.311 Hz |
| 8408.121 Hz | 13477.293 Hz |
| 8424.229 Hz | 13582.122 Hz |
| 8428.313 Hz | 13636.082 Hz |
| 8430.142 Hz | 13717.221 Hz |
| 8435.451 Hz | 13756.503 Hz |
| 8486.421 Hz | 13825.295 Hz |
| 8492.797 Hz | 13829.195 Hz |
| 8548.324 Hz | 14188.611 Hz |
| 8554.361 Hz | 14410.949 Hz |
| 8562.965 Hz | 14436.201 Hz |
| 8578.193 Hz | 14528.429 Hz |
| 8579.323 Hz | 14537.218 Hz |
| 8579.333 Hz | 14563.821 Hz |
| 8597.409 Hz | 14835.809 Hz |
| 8642.181 Hz | 14947.184 Hz |
| 8655.818 Hz | 14948.323 Hz |
| 8758.341 Hz | 15429.139 Hz |
| 8779.323 Hz | 15443.309 Hz |
| 8792.231 Hz | 15450.183 Hz |
| 8819.127 Hz | 16026.221 Hz |
| 8831.132 Hz | 16062.401 Hz |
| 8863.232 Hz | 16081.291 Hz |
| 9028.031 Hz | 16144.343 Hz |
| 9049.205 Hz | 16331.323 Hz |
| 9173.264 Hz | 17316.328 Hz |
| 9175.311 Hz | 17930.967 Hz |
| 9184.338 Hz | 17932.432 Hz |
| 9186.919 Hz | 17951.395 Hz |
| 9393.946 Hz | 17970.122 Hz |

-continued 18242.181 Hz
18254.323 Hz
18265.238 Hz
18337.222 Hz
18344.212 Hz
18378.321 Hz
18921.415 Hz
18926.951 Hz
18931.327 Hz
19124.197 Hz
19133.123 Hz
19321.231 Hz
19686.593 Hz
114508.332 Hz;

(4) frequencies for treatment of prostate cancer as follows 331.3 Hz
331.358 Hz
403.218 Hz
430.439 Hz
436.231 Hz
461.233 Hz
522.2 Hz
522.213 Hz
618.4 Hz
618.407 Hz
618.8 Hz
656.295 Hz
657.394 Hz
657.397 Hz
657.4 Hz
657.483 Hz
659.033 Hz
694.4 Hz
694.689 Hz
694.7 Hz
741.4 Hz
741.421 Hz
749.221 Hz
752.9 Hz
752.933 Hz
776.194 Hz
785.219 Hz
786.332 Hz
793.331 Hz
809.205 Hz
819.322 Hz
840.133 Hz
844.8 Hz
844.822 Hz
847.332 Hz
929.1 Hz
1083.309 Hz
1102.635 Hz
1102.71 Hz
1240.336 Hz
1372.934 Hz
1444.288 Hz
1486.322 Hz
1563.332 Hz
1591.322 Hz
1670.699 Hz
1697.321 Hz
1708.195 Hz
1741.939 Hz
1743.521 Hz
2031.448 Hz
2050.282 Hz
2076.519 Hz
2156.332 Hz
2229.515 Hz
2243.121 Hz
2381.443 Hz
2440.489 Hz
2475.912 Hz
2477.919 Hz -continued 2551.332 Hz
2579.435 Hz
2628.324 Hz
2669.328 Hz
2824.832 Hz
2887.829 Hz
2891.331 Hz
3081.523 Hz
3133.309 Hz
3249.529 Hz
3250.125 Hz
3251.815 Hz
3264.827 Hz
3278.329 Hz
3281.432 Hz
3348.783 Hz
3519.118 Hz
3539.962 Hz
3551.318 Hz
3556.439 Hz
3572.321 Hz
3615.223 Hz
3670.129 Hz
3681.341 Hz
3686.021 Hz
3753.382 Hz
3774.923 Hz
3867.692 Hz
3909.333 Hz
3916.321 Hz
4031.233 Hz
4031.933 Hz
4038.203 Hz
4047.233 Hz
4066.222 Hz
4081.743 Hz
4084.319 Hz
4139.322 Hz
4153.192 Hz
4223.795 Hz
4231.221 Hz
4241.321 Hz
4320.513 Hz
4329.152 Hz
4380.321 Hz
4417.312 Hz
4489.452 Hz
4549.808 Hz
4558.306 Hz
4579.324 Hz
4638.293 Hz
4740.322 Hz
4854.318 Hz
4882.322 Hz
4978.822 Hz
5237.152 Hz
5264.222 Hz
5289.195 Hz
5426.323 Hz
5431.542 Hz
5455.593 Hz
6168.131 Hz
6345.332 Hz
6347.433 Hz
6363.284 Hz
6418.331 Hz
6496.231 Hz
6538.295 Hz
6577.421 Hz
6590.328 Hz
6651.276 Hz
6706.431 Hz
6743.322 Hz
6783.282 Hz
6850.197 Hz
6855.286 Hz
6864.896 Hz
6871.943 Hz
6878.356 Hz -continued 6898.489 Hz
6973.393 Hz
7118.332 Hz
7120.932 Hz
7143.231 Hz
7146.509 Hz
7192.505 Hz
7251.309 Hz
7251.322 Hz
7278.124 Hz
7278.933 Hz
7279.335 Hz
7299.119 Hz
7527.229 Hz
7589.925 Hz
7699.193 Hz
7832.331 Hz
7842.184 Hz
7852.393 Hz
7872.333 Hz
8023.32 Hz
8096.939 Hz
8245.801 Hz
8315.291 Hz
8357.305 Hz
8408.121 Hz
8432.209 Hz
8535.238 Hz
8552.431 Hz
8585.224 Hz
8923.361 Hz
8935.752 Hz
9015.253 Hz
9018.233 Hz
9068.231 Hz
9137.232 Hz
9156.321 Hz
9351.931 Hz
9393.946 Hz
9694.179 Hz
9984.405 Hz
10226.223 Hz
10390.232 Hz
10442.221 Hz
10449.343 Hz
10459.084 Hz
10514.768 Hz
10651.311 Hz
10689.339 Hz
10772.419 Hz
10818.452 Hz
10843.543 Hz
11118.322 Hz
11165.239 Hz
11985.353 Hz
12209.329 Hz
12308.321 Hz
12489.233 Hz
12583.339 Hz
13820.329 Hz
14013.123 Hz
14129.213 Hz
14171.434 Hz
14681.329 Hz
14759.131 Hz
14986.794 Hz
15930.249 Hz
16026.623 Hz
16888.912 Hz
17091.189 Hz
17880.954 Hz
18021.222 Hz
18053.233 Hz
18247.532 Hz
18282.211 Hz
18610.232 Hz
18629.328 Hz
19469.318 Hz
19766.218 Hz -continued 20159.434 Hz
21643.232 Hz
23022.481 Hz
23035.132 Hz
26718.23 Hz
30583.383 Hz
30653.323 Hz
30843.222 Hz
36065.221 Hz
60317.352 Hz;

(5) frequencies for treatment of kidney cancer as follows 628.321 Hz
631.141 Hz
643.312 Hz
812.512 Hz
826.321 Hz
1240.336 Hz
1372.934 Hz
2082.241 Hz
2156.931 Hz
2254.329 Hz
2286.5 Hz
3555.209 Hz
3928.343 Hz
4329.152 Hz
4420.932 Hz
4819.228 Hz
4828.321 Hz
5314.322 Hz
6007.332 Hz
7054.279 Hz
7074.429 Hz
7254.343 Hz
8041.289 Hz
8727.224 Hz
8760.983 Hz
8831.132 Hz
8870.228 Hz
8923.1 Hz
10565.321 Hz
10586.229 Hz
10634.293 Hz
10687.949 Hz
11421.933 Hz
11523.212 Hz
11561.221 Hz
11846.212 Hz
12631.331 Hz
12693.272 Hz
14411.321 Hz
20178.941 Hz;

(6) frequencies for treatment of thyroid cancer as follows 410.231 Hz
412.209 Hz
479.222 Hz
493.442 Hz
517.202 Hz
556.233 Hz
617.313 Hz
618.407 Hz
618.813 Hz
618.927 Hz
621.321 Hz
628.321 Hz
648.252 Hz
658.191 Hz
663.407 Hz
694.689 Hz
777.432 Hz
812.512 Hz

| | |
|---|---|
| 814.251 Hz | 4744.424 Hz |
| 820.907 Hz | 4827.642 Hz |
| 821.202 Hz | 4854.318 Hz |
| 831.223 Hz | 4865.421 Hz |
| 874.341 Hz | 4897.212 Hz |
| 914.429 Hz | 5323.192 Hz |
| 941.311 Hz | 5324.123 Hz |
| 942.331 Hz | 5548.879 Hz |
| 983.429 Hz | 5711.283 Hz |
| 1127.239 Hz | 5730.432 Hz |
| 1191.341 Hz | 5754.332 Hz |
| 1380.828 Hz | 5881.295 Hz |
| 1552.123 Hz | 5924.221 Hz |
| 1587.811 Hz | 6455.131 Hz |
| 1614.409 Hz | 6558.342 Hz |
| 1723.389 Hz | 6620.132 Hz |
| 1771.402 Hz | 6666.839 Hz |
| 2155.311 Hz | 6675.951 Hz |
| 2179.231 Hz | 6714.189 Hz |
| 2185.282 Hz | 6745.333 Hz |
| 2221.323 Hz | 6766.281 Hz |
| 2228.832 Hz | 6779.088 Hz |
| 2315.888 Hz | 6780.679 Hz |
| 2341.312 Hz | 6884.432 Hz |
| 2445.123 Hz | 6917.194 Hz |
| 2454.232 Hz | 6946.928 Hz |
| 2723.302 Hz | 7036.122 Hz |
| 2740.384 Hz | 7083.191 Hz |
| 2749.323 Hz | 7230.838 Hz |
| 2856.253 Hz | 7323.209 Hz |
| 2856.921 Hz | 7355.378 Hz |
| 2859.495 Hz | 7432.143 Hz |
| 2871.795 Hz | 7495.763 Hz |
| 2886.232 Hz | 7505.282 Hz |
| 2928.911 Hz | 7534.221 Hz |
| 2988.212 Hz | 7577.421 Hz |
| 3021.122 Hz | 7623.184 Hz |
| 3078.275 Hz | 7626.332 Hz |
| 3080.592 Hz | 7725.339 Hz |
| 3186.331 Hz | 7726.085 Hz |
| 3198.323 Hz | 7920.879 Hz |
| 3248.321 Hz | 8013.953 Hz |
| 3271.329 Hz | 8019.912 Hz |
| 3284.192 Hz | 8021.331 Hz |
| 3335.332 Hz | 8040.231 Hz |
| 3432.343 Hz | 8078.955 Hz |
| 3434.911 Hz | 8082.173 Hz |
| 3440.212 Hz | 8147.1 Hz |
| 3475.216 Hz | 8281.259 Hz |
| 3509.522 Hz | 8309.752 Hz |
| 3533.328 Hz | 8311.371 Hz |
| 3610.203 Hz | 8435.094 Hz |
| 3637.085 Hz | 8442.293 Hz |
| 3682.489 Hz | 8505.312 Hz |
| 3789.288 Hz | 8521.311 Hz |
| 3822.392 Hz | 8525.789 Hz |
| 3909.333 Hz | 8537.321 Hz |
| 3917.211 Hz | 8540.329 Hz |
| 4023.33 Hz | 8543.211 Hz |
| 4028.204 Hz | 8553.329 Hz |
| 4043.332 Hz | 8744.527 Hz |
| 4046.321 Hz | 8881.819 Hz |
| 4154.301 Hz | 9009.329 Hz |
| 4207.322 Hz | 9068.311 Hz |
| 4226.263 Hz | 9070.809 Hz |
| 4236.945 Hz | 9085.911 Hz |
| 4243.393 Hz | 9535.393 Hz |
| 4261.228 Hz | 9720.412 Hz |
| 4330.289 Hz | 10020.521 Hz |
| 4340.833 Hz | 10039.109 Hz |
| 4347.125 Hz | 10127.279 Hz |
| 4358.333 Hz | 10134.161 Hz |
| 4366.294 Hz | 10257.324 Hz |
| 4426.387 Hz | 10498.339 Hz |
| 4440.962 Hz | 10765.224 Hz |
| 4458.339 Hz | 10849.412 Hz |
| 4478.443 Hz | 10924.342 Hz |
| 4479.113 Hz | 10976.321 Hz |
| 4486.193 Hz | 11030.418 Hz |

11360.332 Hz
11537.292 Hz
11559.292 Hz
11812.119 Hz
11913.222 Hz
11927.934 Hz
11955.949 Hz
11960.179 Hz
12120.049 Hz
12139.222 Hz
12146.335 Hz
12489.233 Hz
12984.462 Hz
13425.229 Hz
13636.082 Hz
13654.272 Hz
13677.211 Hz
14014.941 Hz
14228.295 Hz
14445.214 Hz
14540.932 Hz
14823.325 Hz
14826.334 Hz
14910.894 Hz
15180.492 Hz
15561.322 Hz
15597.284 Hz
16023.119 Hz
16048.391 Hz
16080.831 Hz
16129.321 Hz
16539.532 Hz
17222.225 Hz
17253.222 Hz
17323.196 Hz
17461.504 Hz
17577.221 Hz
17671.321 Hz
17881.709 Hz
17911.323 Hz
17913.286 Hz
17937.203 Hz
17948.264 Hz
18036.921 Hz
18715.412 Hz
19859.429 Hz
21425.321 Hz
21452.445 Hz;

(7) frequencies for treatment of bladder cancer as follows 623.243 Hz
757.084 Hz
870.4 Hz
2454.423 Hz
2480.191 Hz
2581.101 Hz
2715.232 Hz
3042.012 Hz
3196.194 Hz
3265.323 Hz
3438.109 Hz
3692.319 Hz
3952.308 Hz
5230.227 Hz
6022.942 Hz
6061.711 Hz
6710.899 Hz
6721.912 Hz
7181.784 Hz
7212.826 Hz
7458.209 Hz
8235.21 Hz
8749.232 Hz
8767.189 Hz
9354.812 Hz
9611.339 Hz 12532.729 Hz
13467.209 Hz
13777.9 Hz
14015.241 Hz
18524.419 Hz;

(8) frequencies for treatment of colon cancer as follows 78.76 Hz
796.562 Hz
841.541 Hz
842.783 Hz
914.429 Hz
1162.117 Hz
1372.207 Hz
1372.934 Hz
1718.532 Hz
2243.169 Hz
2278.312 Hz
2286.5 Hz
2286.519 Hz
2334.178 Hz
2423.292 Hz
2454.423 Hz
2464.229 Hz
2598.853 Hz
2623.048 Hz
3131.123 Hz
3161.465 Hz
3175.313 Hz
3249.529 Hz
3363.229 Hz
3373.892 Hz
3390.925 Hz
3409.179 Hz
3432.274 Hz
3509.522 Hz
3531.422 Hz
3533.328 Hz
3766.296 Hz
4040.839 Hz
4081.022 Hz
4123.953 Hz
4146.274 Hz
4233.822 Hz
4282.332 Hz
4318.222 Hz
4344.082 Hz
4416.221 Hz
4481.242 Hz
4724.263 Hz
4751.319 Hz
4755.323 Hz
4788.485 Hz
5149.331 Hz
5217.402 Hz
5386.212 Hz
5407.192 Hz
5426.323 Hz
5496.434 Hz
5555.212 Hz
5572.032 Hz
5634.933 Hz
5724.231 Hz
5758.378 Hz
5787.342 Hz
5948.897 Hz
5967.448 Hz
5976.825 Hz
6182.322 Hz
6292.379 Hz
6324.493 Hz
6341.248 Hz
6471.322 Hz
6477.218 Hz
6558.342 Hz
6855.286 Hz 7129.843 Hz
7140.187 Hz
7162.422 Hz
7368.222 Hz
7645.859 Hz
7829.234 Hz
7866.229 Hz
7877.334 Hz
8013.314 Hz
8374.942 Hz
8384.228 Hz
8408.121 Hz
8534.111 Hz
8568.033 Hz
8573.122 Hz
9226.222 Hz
9351.9 Hz
9737.211 Hz
9744.193 Hz
9942.321 Hz
10301.371 Hz
10401.515 Hz
10872.693 Hz
11220.222 Hz
11283.378 Hz
12256.432 Hz
13749.858 Hz
15231.548 Hz
15248.324 Hz
58191.928 Hz
60317.352 Hz;

(9) frequencies for treatment of pancreas cancer as follows 331.3 Hz
331.365 Hz
436.3 Hz
436.332 Hz
447.942 Hz
476.127 Hz
559.292 Hz
589.187 Hz
624.218 Hz
727 Hz
734.921 Hz
809.313 Hz
845.309 Hz
870.4 Hz
963.221 Hz
1156.79 Hz
1157 Hz
1179 Hz
1360.133 Hz
1372.207 Hz
1372.934 Hz
1804.126 Hz
1816.221 Hz
1873.477 Hz
1967.211 Hz
1990.482 Hz
2278.312 Hz
2315.921 Hz
2320.315 Hz
2334.178 Hz
2381.443 Hz
2469 Hz
2477.919 Hz
2542.221 Hz
2598.853 Hz
2647.938 Hz
2685.081 Hz
2716.095 Hz
2721.331 Hz
2732.231 Hz
2809.849 Hz
2823.428 Hz
2835.332 Hz
3134.313 Hz
3241.461 Hz
3255.219 Hz
3263.432 Hz
3286.255 Hz
3330.935 Hz
3373.892 Hz
3438.109 Hz
3449.219 Hz
3535.219 Hz
3549.215 Hz
3564.419 Hz
3619.412 Hz
3622.312 Hz
3638.432 Hz
3696.424 Hz
3943.214 Hz
3976.929 Hz
4014.889 Hz
4041.219 Hz
4044.195 Hz
4056.384 Hz
4085.971 Hz
4144.592 Hz
4153.192 Hz
4161.889 Hz
4243.393 Hz
4332.498 Hz
4341.423 Hz
4355.327 Hz
4417.885 Hz
4422.322 Hz
4451.297 Hz
4486.384 Hz
4558.306 Hz
4580 Hz
4685.082 Hz
4839.589 Hz
5151.402 Hz
5209.911 Hz
5262.282 Hz
5271.312 Hz
5387.73 Hz
5494.928 Hz
5521.221 Hz
5573.209 Hz
5609.382 Hz
5929.616 Hz
5948.897 Hz
5966.112 Hz
5976.825 Hz
6064.197 Hz
6086.256 Hz
6157.253 Hz
6215.298 Hz
6333.917 Hz
6365.242 Hz
6558.342 Hz
6568.278 Hz
6823.194 Hz
6853.391 Hz
6855.286 Hz
7213.204 Hz
7228.528 Hz
7238.232 Hz
7277.921 Hz
7280.422 Hz
7320.494 Hz
7366.412 Hz
7534.221 Hz
7548.713 Hz
7567.127 Hz
7620.851 Hz
7663.209 Hz
7725.203 Hz
7852.233 Hz
7920.879 Hz
7985.122 Hz
8008.323 Hz 8013.312 Hz
8045.484 Hz
8242.332 Hz
8351.622 Hz
8408.121 Hz
8455.894 Hz
8551.231 Hz
8743.321 Hz
8789.631 Hz
8868.809 Hz
9012.241 Hz
9028.994 Hz
9131.232 Hz
9658.296 Hz
9663.495 Hz
9680.737 Hz
9824.442 Hz
9942.321 Hz
10279.122 Hz
10388.49 Hz
10438.495 Hz
10518.311 Hz
10528.239 Hz
10582.095 Hz
10926.111 Hz
10948.411 Hz
10955.558 Hz
11538.193 Hz
11904.741 Hz
12255.229 Hz
12613.341 Hz
12819.942 Hz
13674.482 Hz
13731.322 Hz
14525.312 Hz
14537.218 Hz
14549.331 Hz
14845.453 Hz
14944.989 Hz
15246.315 Hz
18668.239 Hz
19321.231 Hz
19347.208 Hz
30182.932 Hz;

(10) frequencies for treatment of lung cancer as follows 304.148 Hz
694.7 Hz
694.727 Hz
708.8 Hz
708.841 Hz
1587.811 Hz
1759.318 Hz
1873.477 Hz
2253.704 Hz
2391.312 Hz
2454.232 Hz
2729.929 Hz
2741.261 Hz
2761.312 Hz
2784.491 Hz
2812.443 Hz
2855.218 Hz
2859.495 Hz
3128.822 Hz
3139.297 Hz
3193.212 Hz
3348.783 Hz
3360.971 Hz
3366.311 Hz
3373.892 Hz
3440.212 Hz
3461.322 Hz
3682.489 Hz
3727.231 Hz
3749.882 Hz 3769.942 Hz
4131.235 Hz
4158.393 Hz
4243.393 Hz
4347.733 Hz
4373.411 Hz
4378.321 Hz
4416.221 Hz
4481.242 Hz
4777.521 Hz
4798.422 Hz
4837.241 Hz
4959.842 Hz
5013.321 Hz
5047.523 Hz
5068.322 Hz
5371.922 Hz
5538.432 Hz
5548.879 Hz
5679.309 Hz
5734.143 Hz
5787.342 Hz
6445.309 Hz
6838.434 Hz
6870.955 Hz
6879.216 Hz
7079.411 Hz
7216.288 Hz
7376.089 Hz
7761.289 Hz
8082.173 Hz
8281.259 Hz
8352.189 Hz
8442.473 Hz
8773.916 Hz
8935.752 Hz
9121.223 Hz
9181.434 Hz
9317.913 Hz
9363.896 Hz
9736.919 Hz
9753.321 Hz
10424.908 Hz
10452.913 Hz
10824.609 Hz
11656.329 Hz
12748.919 Hz
15774.291 Hz
15798.333 Hz
16510.333 Hz;

(11) frequencies for treatment of leiomyosarcoma as follows 836.923 Hz
843.181 Hz
1411.241 Hz
2073.721 Hz
2381.443 Hz
2711.019 Hz
2911.329 Hz
3232.185 Hz
3518.321 Hz
3544.209 Hz
3569.219 Hz
4233.822 Hz
4241.321 Hz
4266.591 Hz
4337.322 Hz
4424.112 Hz
4436.111 Hz
4485.22 Hz
5545.521 Hz
5577.841 Hz
5631.422 Hz
5696.184 Hz
6472.098 Hz
6558.342 Hz 6651.276 Hz
7168.892 Hz
7406.309 Hz
7452.528 Hz
7649.209 Hz
7808.352 Hz
9040.313 Hz
9074.294 Hz
9189.092 Hz
9484.512 Hz
9943.972 Hz
12086.394 Hz;

(12) frequencies for treatment of mesothelioma as follows 958.929 Hz
1713.913 Hz
1736.782 Hz
2334.178 Hz
2607.193 Hz
3112.974 Hz
3319.945 Hz
3449.219 Hz
3622.312 Hz
5151.402 Hz
5887.022 Hz
5965.922 Hz
6516.793 Hz
7224.197 Hz
9471.152 Hz
14617.393 Hz;

(13) frequencies for treatment of neuro-endocrine as follows 1766.335 Hz
2408.225 Hz
2441.502 Hz
2647.938 Hz
2741.261 Hz
3020.212 Hz
3128.822 Hz
3238.742 Hz
3296.431 Hz
3348.783 Hz
3360.971 Hz
3440.212 Hz
3533.328 Hz
3666.283 Hz
4079.282 Hz
4243.393 Hz
4426.387 Hz
5245.818 Hz
5536.242 Hz
5548.879 Hz
5739.422 Hz
5849.241 Hz
6291.631 Hz
6406.891 Hz
6780.679 Hz
7151.264 Hz
7482.245 Hz
7575.393 Hz
8359.932 Hz
9073.418 Hz;

(14) frequencies for treatment of leukemia and chronic lymphoid cancer as follows 814.413 Hz
825.145 Hz
2415.243 Hz
2436.316 Hz
2874.432 Hz
2891.029 Hz
3361.671 Hz
5245.452 Hz
5557.333 Hz
6850.197 Hz
6919.322 Hz
7587.224 Hz
7629.318 Hz
8172.405 Hz
8272.338 Hz
8438.453 Hz
12950.331 Hz;

(15) frequencies for treatment of myeloma as follows 765.196 Hz
2336.238 Hz
2372.122 Hz
2381.443 Hz
2425.394 Hz
2656.339 Hz
2741.261 Hz
2883.618 Hz
2919.273 Hz
3265.323 Hz
3564.455 Hz
3580.25 Hz
3584.291 Hz
3674.292 Hz
5249.331 Hz
7967.311 Hz
7973.125 Hz
8049.952 Hz
8283.329 Hz
10351.323 Hz;

(16) frequencies for treatment of lymphoma as follows 752.5 Hz
976.3 Hz
1558.223 Hz
2310.912 Hz
2477.919 Hz
2560.843 Hz
3348.783 Hz
3371.216 Hz
3605.432 Hz
3623.198 Hz
3838.281 Hz
3838.48 Hz
5102 Hz
5696.932 Hz
5724.231 Hz
6358.194 Hz
7472.211 Hz
8062.121 Hz
8222.222 Hz;

and (17) frequencies for treatment of brain cancer as follows 1372.934 Hz
2318.182 Hz
2381.443 Hz
2425.394 Hz
2442.423 Hz
2478.973 Hz
2654.513 Hz
2661.324 Hz
2686.105 Hz
2690.179 Hz
3249.332 Hz -continued

| | |
|---|---|
| 3277.509 | Hz |
| 3335.279 | Hz |
| 3348.783 | Hz |
| 3436.211 | Hz |
| 3916.321 | Hz |
| 4031.933 | Hz |
| 4086.091 | Hz |
| 4241.321 | Hz |
| 4318.222 | Hz |
| 4334.33 | Hz |
| 4358.333 | Hz |
| 4393.419 | Hz |
| 4454.194 | Hz |
| 4515.789 | Hz |
| 4619.324 | Hz |
| 4723.937 | Hz |
| 4853.286 | Hz |
| 5289.231 | Hz |
| 5378.099 | Hz |
| 5426.323 | Hz |
| 5640.981 | Hz |
| 6316.211 | Hz |
| 6459.203 | Hz |
| 6474.332 | Hz |
| 6626.572 | Hz |
| 6855.286 | Hz |
| 6915.886 | Hz |
| 6943.386 | Hz |
| 7151.264 | Hz |
| 7182.922 | Hz |
| 7194.897 | Hz |
| 7323.209 | Hz |
| 7390.343 | Hz |
| 7796.221 | Hz |
| 7961.122 | Hz |
| 8128.942 | Hz |
| 8245.109 | Hz |
| 8272.281 | Hz |
| 8358.154 | Hz |
| 8408.121 | Hz |
| 9138.82 | Hz |
| 10719.318 | Hz |
| 11556.241 | Hz |
| 12828.633 | Hz |
| 14515.962 | Hz |
| 14586.765 | Hz. |

2. The system according to claim 1, wherein the frequencies of the amplitude modulations generated are controllable to within an accuracy of 100 parts per million relative to the determined or predetermined reference amplitude modulation frequencies.

3. The system according to claim 2, wherein the frequencies of the amplitude modulations generated are controllable to within an accuracy of 10 parts per million relative to the determined or predetermined reference amplitude modulation frequencies.

4. The system according to claim 3, wherein the frequencies of the amplitude modulations generated are controllable to within an accuracy of about 1 parts per million relative to the determined or predetermined reference amplitude modulation frequencies.

5. The system according to claim 1, wherein the one or more amplitude modulated low energy emissions generated are maintained at a stability during emission of at least $10^{-5}$.

6. The system according to claim 5, wherein a stability of at least $10^{-6}$ is maintained.

7. The system according to claim 6, wherein a stability of at least $10^{-7}$ is maintained.

8. The system according to claim 1, wherein said at least one controllable generator circuit is controllable by amplitude modulation control signals which lead to various forms of amplitude modulation wave forms being generated.

9. The system according to claim 8, wherein the amplitude modulation wave forms are selected from sinusoidal, square, triangular or multiple combinations thereof.

10. The system according to claim 8, wherein the at least one generator circuit is controllable by amplitude modulation control signals which generate a plurality of amplitude modulation wave forms, either sequentially or simultaneously.

11. The system according to claim 1, wherein the one or more high frequency carrier signals generated by the at least one generator circuit are selected from one or more high frequencies selected from about 27 MHz, 433 MHz and 900 MHz.

12. The system according to claim 1, wherein the system further comprises one or more interfaces communicating with the at least one data processor, and wherein the control information is transferable to said one or more interfaces and hence to the at least one data processor to enable command signals responsive to received control information to be communicated to the at least one generator circuit by the at least one data processor.

13. The system according to claim 12, wherein the control information is transferable over a communication link to the at least one data processor via the one or more interfaces communicating with the at least one data processor.

14. The system according to claim 12, wherein the control information is stored in an information storage device and wherein the control information is transferable to the at least one data processor via said one or more interfaces communicating with the at least one data processor.

15. The system according to claim 12, wherein the system further comprises a user identification device communicating with at least one of the at least one data processor to enable the system to be activated for use only by the user.

16. The system according to claim 1,
further comprising a monitor comprising monitoring software for monitoring the amplitude and the amplitude modulation frequency of the amplitude modulated low energy electromagnetic emissions generated by the at least one generator circuit.

17. The system according to claim 1, wherein the determined or predetermined amplitude modulation frequency control information is determined or predetermined by a biofeedback process involving observations or measurements of physiological reactions by the subject during a time that cellular functions of the subject are excited by exposing the subject to emissions of high frequency carrier signals amplitude modulated at a series of amplitude modulation frequencies.

18. The system according to claim 17, wherein the determined or predetermined frequencies are employed as a mode to identify a nature of a tumor or cancer harbored by the warm-blooded mammalian subject.

* * * * *